(12) United States Patent
Miyachi et al.

(10) Patent No.: US 8,916,682 B2
(45) Date of Patent: Dec. 23, 2014

(54) LIPID PEPTIDE AND HYDROGEL

(75) Inventors: Nobuhide Miyachi, Tokyo (JP); Takehisa Iwama, Funabashi (JP); Masahiro Gotoh, Fukuoka (JP); Tatsuo Maruyama, Fukuoka (JP); Daisuke Koda, Fukuoka (JP)

(73) Assignees: Nissan Chemical Industries, Ltd., Tokyo (JP); Kyushu University, Fukuoka (JP)

( * ) Notice: Subject to any disclaimer, the term of this patent is extended or adjusted under 35 U.S.C. 154(b) by 548 days.

(21) Appl. No.: 12/452,473
(22) PCT Filed: Jul. 4, 2008
(86) PCT No.: PCT/JP2008/062212
§ 371 (c)(1), (2), (4) Date: May 4, 2010
(87) PCT Pub. No.: WO2009/005151
PCT Pub. Date: Jan. 8, 2009

(65) Prior Publication Data
US 2010/0291210 A1 Nov. 18, 2010

(30) Foreign Application Priority Data
Jul. 5, 2007 (JP) ................. 2007-177538

(51) Int. Cl.
| | | |
|---|---|---|
| A61K 38/04 | (2006.01) |
| C07K 14/50 | (2006.01) |
| C07K 5/107 | (2006.01) |
| C07K 7/06 | (2006.01) |
| C07K 5/103 | (2006.01) |
| C07K 5/11 | (2006.01) |
| C07K 5/117 | (2006.01) |

(52) U.S. Cl.
CPC .............. *C07K 7/06* (2013.01); *C07K 5/1016* (2013.01); *C07K 5/1008* (2013.01); *C07K 5/101* (2013.01); *C07K 5/1019* (2013.01); *C07K 5/1024* (2013.01)
USPC .......................... 530/330; 514/21.8; 514/21.9

(58) Field of Classification Search
CPC ......... A61K 38/08; A61K 38/04; C07K 14/50
See application file for complete search history.

(56) References Cited

U.S. PATENT DOCUMENTS

| 6,027,711 | A * | 2/2000 | Sharma .................. 424/1.69 |
| 6,090,763 | A * | 7/2000 | Stewart et al. ............ 510/130 |
| 2002/0197281 | A1 | 12/2002 | Seiberg et al. |
| 2003/0138388 | A1* | 7/2003 | Seiberg et al. .............. 424/63 |
| 2005/0129633 | A1 | 6/2005 | Lin |
| 2007/0099840 | A1 | 5/2007 | Ulijn et al. |

FOREIGN PATENT DOCUMENTS

| EP | 1 741 421 A1 | 1/2007 |
| JP | A 60-214768 | 10/1985 |
| JP | A 2002-085957 | 3/2002 |
| JP | A 2003-327949 | 11/2003 |
| JP | A 2004-250797 | 9/2004 |
| WO | WO 03/099841 A2 | 12/2003 |
| WO | WO 2005/105029 A1 | 11/2005 |

OTHER PUBLICATIONS

Gilead and Gazit, Self Organization of short peptide fragments: From Amyloid Fibrils to Nanoscale Supramolecular Assemblies, Supramolecular Chemistry, vol. 17 (1-2), p. 87-92, 2005.*
Lowik and Hest, Peptide Based Amphiphiles, Chem. Soc. Rev. vol. 33, pp. 234-245, 2004.*
Infante et. al. Synthesis and surface activity properties of hydrophobic/hydrophilic peptides. Inr. J. Peptide Protein Rev. 43, 1994, 173-179.*
European Search Report issued in European Patent Application No. 08790893.5 dated Aug. 13, 2010.
Huo et al., "Metal Complexation with Langmuir Monolayers of Histidyl Peptide Lipids," *Chemistry—A European Journal*, 2001, pp. 4796-4804, vol. 7, No. 22.
Ozols et al., "Identification of the NH$_2$-terminal Blocking Group of NADH-Cytochrome b$_5$ Reductase as Myristic Acid and the Complete Amino Acid Sequence of the Membrane-binding Domain," The Journal of Biological Chemistry, vol. 259, No. 21, Nov. 10, 1984, pp. 13349-13354.
Infante et al., "Synthesis and surface activity properties of hydrophobic/hydrophilic peptides," Int. J. Peptide Protein Res., vol. 43, 1994, pp. 173-179.
Nastruzzi et al., "Liposomes as carriers for DNA-PNA hybrids," Journal of Controlled Release, vol. 68, 2000, pp. 237-249.
Van Bommel et al., "Responsive Cyclohexane-Based Low-Molecular-Weight Hydrogelators with Modular Architecture," Angew. Chem. Int. Ed., vol. 43, 2004, pp. 1663-1667.
Hartgerink et al., "Self-Assembly and Mineralization of Peptide-Amphiphle Nanofibers," Science, vol. 294, Nov. 23, 2001, pp. 1684-1688.
Petka et al., "Reversible Hydrogels from Self-Assembling Artificial Proteins," Science, vol. 281, Jul. 17, 1998, pp. 389-392.
Aggeli et al., "Self-Assembling Peptide Polyelectrolyte β-Sheet Complexes Form Nematic Hydrogels," Agnew. Chem. Int. Ed., vol. 42, 2003, pp. 5603-5606.

(Continued)

*Primary Examiner* — James H Alstrum Acevedo
*Assistant Examiner* — Jeanette Lieb
(74) *Attorney, Agent, or Firm* — Oliff PLC

(57) ABSTRACT

There is provided a lipid peptide that is capable of forming a hydrogel with an extremely small amount thereof over a liquid property range from acidic to alkaline, and a hydrogel having high environmental suitability, biocompatibility and biodegradability. A lipid peptide represented by Formula (1);

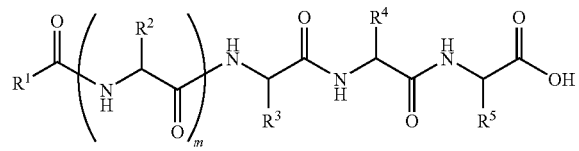

(where $R^1$ represents an aliphatic group having 9 to 23 carbon atoms;
$R^2$, $R^3$, $R^4$ and $R^5$ independently represent a hydrogen atom, an alkyl group having 1 to 7 carbon atom(s) which optionally has a branched chain having 1 to 3 carbon atom(s), a phenylmethyl group, a phenylethyl group or a —$(CH_2)_n$—X group, and at least one of $R^2$, $R^3$, $R^4$ and $R^5$ represents a —$(CH_2)_n$—X group;
n represents the number of 1 to 4; X represents an amino group, a guanidine group, a —$CONH_2$ group or a 5-membered ring, a 6-membered ring or a fused heterocyclic ring composed of a 5-membered ring and a 6-membered ring which optionally have 1 to 3 nitrogen atom(s); and m represents 1 or 2), and a hydrogel comprising the lipid peptide.

1 Claim, 1 Drawing Sheet

(56) References Cited

OTHER PUBLICATIONS

Matsumoto et al., "The Supramolecular-Hydrogel toward 'The Smart Biomaterials,'" DOJIN News, No. 118, 2006, pp. 1-16. (with English-language abstract).

Nguyen-Le et al., "Phramacological hetereogeneity of neurotensin receptors: an in vitro study," Cn. J. Physiol. Phramacol., 1997, vol. 75, No. 6, pp. 547-551.

Ohashi et al., "Application of Arginine-Rich RNA-Binding Peptides to Gene Delivery," Peptide Science, 2000, pp. 241-242.

International Search Report issued in corresponding International Application No. PCT/JP2008/062212, mailed Oct. 7, 2008. (with English-language translation).

Written Opinion of the International Searching Authority issued in corresponding International Application No. PCT/JP2008/062212, mailed Oct. 7, 2008. (with English-language translation).

Aug. 12, 2013 Office Action issued in U.S. Appl. No. 13/685,565.

Jan. 30, 2014 Office Action issued in U.S. Appl. No. 13/685,565.

* cited by examiner

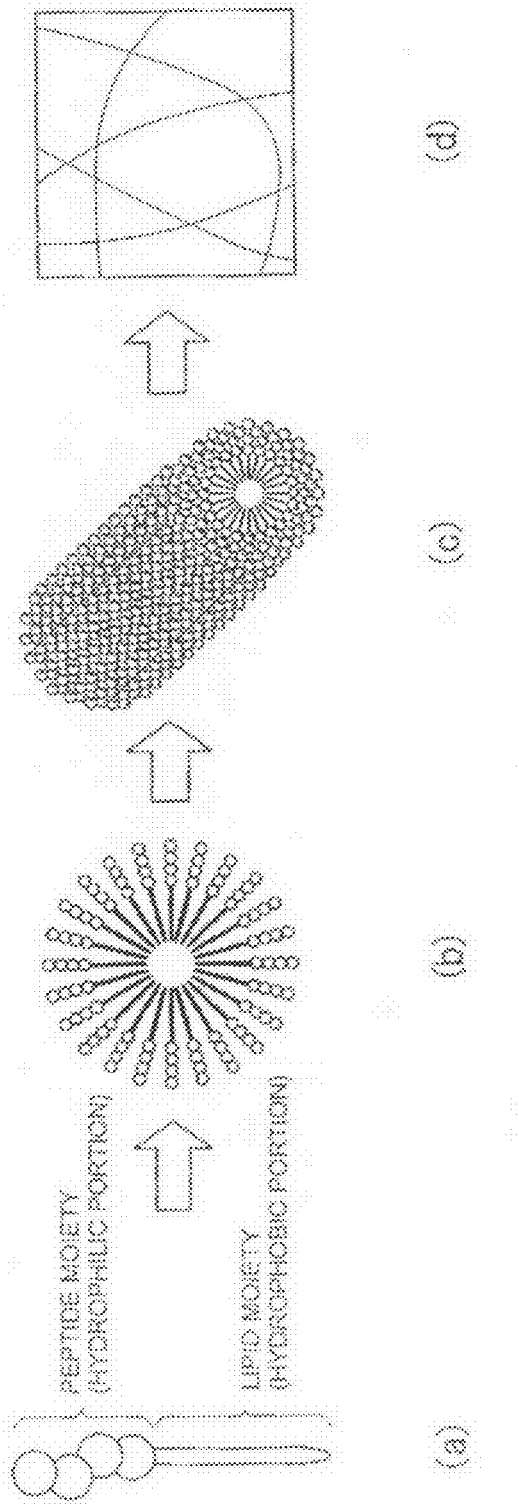

SEQUENCE LISTING

<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: peptide moiety

<400> SEQUENCE: 1

Gly Gly Gly His
1

<210> SEQ ID NO 2
<211> LENGTH: 4
<212> TYPE: PRT
<213> ORGANISM: Artificial Sequence
<220> FEATURE:
<223> OTHER INFORMATION: peptide moiety

<400> SEQUENCE: 2

Gly Gly His Gly
1

<210> SEQ ID NO 3
<211> LENGTH: 4
<212> TYPE: PRT
<213> ORGANISM: Artificial Sequence
<220> FEATURE:
<223> OTHER INFORMATION: peptide moiety

<400> SEQUENCE: 3

Gly His Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: peptide moiety

<400> SEQUENCE: 4

His Gly Gly Gly
1

<210> SEQ ID NO 5
<211> LENGTH: 4
<212> TYPE: PRT
<213> ORGANISM: Artificial Sequence
<220> FEATURE:
<223> OTHER INFORMATION: peptide moiety

<400> SEQUENCE: 5

Gly Gly Gly Lys
1

<210> SEQ ID NO 6
<211> LENGTH: 4
<212> TYPE: PRT
<213> ORGANISM: Artificial Sequence
<220> FEATURE:
<223> OTHER INFORMATION: peptide moiety

<400> SEQUENCE: 6

Gly Gly Lys Gly
1

```
<210> SEQ ID NO 7
<211> LENGTH: 4
<212> TYPE: PRT
<213> ORGANISM: Artificial Sequence
<220> FEATURE:
<223> OTHER INFORMATION: peptide moiety

<400> SEQUENCE: 7

Gly Lys Gly Gly
1

<210> SEQ ID NO 8
<211> LENGTH: 4
<212> TYPE: PRT
<213> ORGANISM: Artificial Sequence
<220> FEATURE:
<223> OTHER INFORMATION: peptide moiety

<400> SEQUENCE: 8

Lys Gly Gly Gly
1

<210> SEQ ID NO 9
<211> LENGTH: 4
<212> TYPE: PRT
<213> ORGANISM: Artificial Sequence
<220> FEATURE:
<223> OTHER INFORMATION: peptide moiety

<400> SEQUENCE: 9

Gly Gly Gly Trp
1

<210> SEQ ID NO 10
<211> LENGTH: 4
<212> TYPE: PRT
<213> ORGANISM: Artificial Sequence
<220> FEATURE:
<223> OTHER INFORMATION: peptide moiety

<400> SEQUENCE: 10

Gly Gly Trp Gly
1

<210> SEQ ID NO 11
<211> LENGTH: 4
<212> TYPE: PRT
<213> ORGANISM: Artificial Sequence
<220> FEATURE:
<223> OTHER INFORMATION: peptide moiety

<400> SEQUENCE: 11

Gly Trp Gly Gly
1

<210> SEQ ID NO 12
<211> LENGTH: 4
<212> TYPE: PRT
<213> ORGANISM: Artificial Sequence
<220> FEATURE:
<223> OTHER INFORMATION: peptide moiety

<400> SEQUENCE: 12

Trp Gly Gly Gly
1
```

```
<210> SEQ ID NO 13
<211> LENGTH: 4
<212> TYPE: PRT
<213> ORGANISM: Artificial Sequence
<220> FEATURE:
<223> OTHER INFORMATION: peptide moiety

<400> SEQUENCE: 13

Gly Gly Gly Arg
1

<210> SEQ ID NO 14
<211> LENGTH: 4
<212> TYPE: PRT
<213> ORGANISM: Artificial Sequence
<220> FEATURE:
<223> OTHER INFORMATION: peptide moiety

<400> SEQUENCE: 14

Gly Gly Gly Gln
1

<210> SEQ ID NO 15
<211> LENGTH: 4
<212> TYPE: PRT
<213> ORGANISM: Artificial Sequence
<220> FEATURE:
<223> OTHER INFORMATION: peptide moiety

<400> SEQUENCE: 15

Gly Gly Gly Asn
1

<210> SEQ ID NO 16
<211> LENGTH: 4
<212> TYPE: PRT
<213> ORGANISM: Artificial Sequence
<220> FEATURE:
<223> OTHER INFORMATION: peptide moiety

<400> SEQUENCE: 16

Gly Gly Phe His
1

<210> SEQ ID NO 17
<211> LENGTH: 4
<212> TYPE: PRT
<213> ORGANISM: Artificial Sequence
<220> FEATURE:
<223> OTHER INFORMATION: peptide moiety

<400> SEQUENCE: 17

Gly Gly Ala His
1

<210> SEQ ID NO 18
<211> LENGTH: 4
<212> TYPE: PRT
<213> ORGANISM: Artificial Sequence
<220> FEATURE:
<223> OTHER INFORMATION: peptide moiety

<400> SEQUENCE: 18

Gly Gly Ile His
1
```

```
<210> SEQ ID NO 19
<211> LENGTH: 4
<212> TYPE: PRT
<213> ORGANISM: Artificial Sequence
<220> FEATURE:
<223> OTHER INFORMATION: peptide moiety

<400> SEQUENCE: 19

Gly Gly Leu His
1

<210> SEQ ID NO 20
<211> LENGTH: 4
<212> TYPE: PRT
<213> ORGANISM: Artificial Sequence
<220> FEATURE:
<223> OTHER INFORMATION: peptide moiety

<400> SEQUENCE: 20

Gly Gly Val His
1

<210> SEQ ID NO 21
<211> LENGTH: 4
<212> TYPE: PRT
<213> ORGANISM: Artificial Sequence
<220> FEATURE:
<223> OTHER INFORMATION: peptide moiety

<400> SEQUENCE: 21

Gly Ala Gly His
1

<210> SEQ ID NO 22
<211> LENGTH: 4
<212> TYPE: PRT
<213> ORGANISM: Artificial Sequence
<220> FEATURE:
<223> OTHER INFORMATION: peptide moiety

<400> SEQUENCE: 22

Gly Val Gly His
1

<210> SEQ ID NO 23
<211> LENGTH: 4
<212> TYPE: PRT
<213> ORGANISM: Artificial Sequence
<220> FEATURE:
<223> OTHER INFORMATION: peptide moiety

<400> SEQUENCE: 23

Gly Leu Gly His
1

<210> SEQ ID NO 24
<211> LENGTH: 4
<212> TYPE: PRT
<213> ORGANISM: Artificial Sequence
<220> FEATURE:
<223> OTHER INFORMATION: peptide moiety

<400> SEQUENCE: 24

Gly Ile Gly His
1

<210> SEQ ID NO 25
```

```
<211> LENGTH: 4
<212> TYPE: PRT
<213> ORGANISM: Artificial Sequence
<220> FEATURE:
<223> OTHER INFORMATION: peptide moiety

<400> SEQUENCE: 25

Ala Gly Gly His
1

<210> SEQ ID NO 26
<211> LENGTH: 4
<212> TYPE: PRT
<213> ORGANISM: Artificial Sequence
<220> FEATURE:
<223> OTHER INFORMATION: peptide moiety

<400> SEQUENCE: 26

Val Gly Gly His
1

<210> SEQ ID NO 27
<211> LENGTH: 5
<212> TYPE: PRT
<213> ORGANISM: Artificial Sequence
<220> FEATURE:
<223> OTHER INFORMATION: peptide moiety

<400> SEQUENCE: 27

Gly Gly Gly Gly His
1               5

<210> SEQ ID NO 28
<211> LENGTH: 5
<212> TYPE: PRT
<213> ORGANISM: Artificial Sequence
<220> FEATURE:
<223> OTHER INFORMATION: peptide moiety

<400> SEQUENCE: 28

Gly Gly Gly Gly Lys
1               5

<210> SEQ ID NO 29
<211> LENGTH: 5
<212> TYPE: PRT
<213> ORGANISM: Artificial Sequence
<220> FEATURE:
<223> OTHER INFORMATION: peptide moiety

<400> SEQUENCE: 29

Gly Gly Gly Gly Trp
1               5
```

LIPID PEPTIDE AND HYDROGEL

TECHNICAL FIELD

The present invention relates to a novel lipid peptide, a fiber formed by the self-assembly of the lipid peptide and a hydrogel composed of the lipid peptide or the fiber and an aqueous solution or an alcohol aqueous solution.

The lipid peptide of the present invention can be particularly suitably utilized as a hydrogelator in the production of various gel form base materials such as cosmetics, gel form food such as agars, and pharmaceutical preparations. In addition, a hydrogel obtained from the lipid peptide is suited for various functional materials for articles of daily use such as cosmetics, (soft) contact lenses, paper diapers and aromatics; dry-land agricultural applications; chemical analysis applications such as chromatography; medicine/pharmacy applications; bio-chemistry field applications such as carriers of protein, cell culture-related base materials, and a bioreactor; and the like.

BACKGROUND ART

The hydrogel contains water as the medium, so that it is useful as a gel having high biocompatibility and is used in various fields such as applications for articles of daily use such as paper diapers, cosmetics and aromatics.

Examples of a related-art hydrogel include natural polymer gels such as agarose, and synthetic polymer gels in which between polymer chains is crosslinked through a chemical covalent bond such as an acrylamide gel.

Recently, functional gels in which various functions such as material retention capacities, an external stimulus responsive performance and a biodegradability in consideration of the environment are imparted to a hydrogel, are attracting attention, and there are performed attempts for developing various functions by introducing functional molecules into the natural or the synthetic polymer gels using a copolymerization reaction or the like.

Thus, for imparting new functions to a hydrogel, it is necessary to study the nanostructure and the surface structure of the gel in detail, however, in the above method for introducing functional molecules using a copolymerization reaction, there are various problems such as problems in which the introduction rate of functional groups is limited and a precise molecule design is difficult, a problem of the safety of materials that remain unreacted, and a problem in which the preparation of the gel is extremely complicated.

As opposed to such a related-art "top-down type" development of functional materials, attracting attention is a "bottom-up type" study for creating functional materials by which atoms or molecules which are the minimum units of the substance are assembled and in the resultant assembly which is a supramolecule, new functions are discovered.

Also in the field of the gel, the development of a novel gel formed from a non-covalent gel fiber (so-called "supramolecule polymer") produced by self-assembly of a low molecular weight compound is progressed. This "self-assembly" refers to such a phenomenon that in a substance (molecule) group in a random state at first, molecules associate spontaneously by an intermolecular non-covalent interaction or the like under an appropriate external condition to grow to a macro functional assembly.

The novel gel is attracting attention, because the control of the macroscopic structure or function thereof is theoretically possible by controlling an intermolecular interaction or a weak non-covalent bond of a molecule assembly according to a molecule design of a monomer.

However, with respect to the way of controlling the intermolecular interaction or non-covalent bond between low molecular weight compounds, there is not yet found an apparent methodology. In addition, in the study of the non-covalent gel, the study of self-assembly utilizing a hydrogen bond in an organic solvent precedes because of a relative easiness of the gel formation, and self-assembled compounds (that is, hydrogelators or the like) in an aqueous solution have been found only accidentally.

Hydrogelators for forming a non-covalent gel which have been repotted until now are broadly divided into the following three categories.

(1. Hydrogelators Having an Amphipathic Low Molecular Weight Molecule as the Skeleton Thereof)

This hydrogelator is created with an artificial lipid layer as a model and examples of the agent include surfactant-type gelling agents having a quaternary ammonium salt portion as a hydrophilic portion and having an alkyl long chain as a hydrophobic portion, and amphoteric surfactant-type gelling agents in which hydrophilic portions of two surfactant-type molecules are coupled.

As one example of the hydrogel formed by such gelling agents, there is disclosed a molecule organizational hydrogel formed by adding an anion having a molecular mass of 90 or more to a dispersion aqueous solution of a cationic amphipathic compound having a branched alkyl group in the hydrophobic portion (Patent Document 1).

(2. Hydrogelators Having a Skeleton in the Motif of Intravital Components)

Examples of this type of hydrogelators include gelling agents utilizing an association between molecule-assemblies through a peptide secondary structure skeleton (such as α-helix structure and β-sheet structure).

For example, there are disclosed a gelling agent having an α-helix structure (Non-patent Document 1) and a gelling agent having β-sheet structure (Non-patent Document 2).

(3. Hydrogelators Having a Semi-Artificial Low Molecular Weight Molecule as the Skeleton Thereof)

This type of hydrogelators is composed of a combination of intravital components (hydrophilic portion) such as DNA bases, peptide chains and sugar chains and alkyl chains (hydrophobic portion) and the like, and can be referred to as a gelling agent combining characteristics of the above two types of gelling agents. Here, the DNA base, the peptide chain and the sugar chain assume not only a role of enhancing the hydrophilicity, but also a role of imparting an intermolecular interaction such as a hydrogen bond.

For example, there are disclosed a hydrogelator containing a glycoside amino acid derivative having a sugar structure site having an N-acetylated glycoside structure of a monosaccharide or disaccharide (Patent Document 2) and disclosed a fine hollow fiber formed having a self-assembling property from a peptide lipid represented by General Formula: RCO(NHCH$_2$CO)$_m$OH and a transition metal (Patent Document 3).

In addition, it is disclosed that an amphipathic peptide having a structure of (hydrophobic portion-cysteine residue (forming a disulfide bond during the network formation)-glycerin residue (imparting flexibility)-phosphorylated serin residue-cell adhesive peptide) forms a β-sheet type fiber network with the hydrophobic portion as a nucleus (Non-patent Document 3).

In addition, there is also disclosed a case where a sugar lipid-type supramolecule hydrogel was produced using a chemical library (Non-patent Document 4).

[Patent Document 1]
 Japanese Patent Application Publication No. JP-A-2002-085957
[Patent Document 2]
 Japanese Patent Application Publication No. JP-A-2003-327949
[Patent Document 3]
 Japanese Patent Application Publication No. JP-A-2004-250797
[Non-patent Document 1]
 W. A. Pekata et al., SCIENCE, vol. 281, 389 (1998)
[Non-patent Document 2]
 A. Aggeli et al., Angew. Chem. Int. Ed., vol. 42, 5603-5606 (2003)
[Non-patent Document 3]
 Jeffrey D. Hartgerink, Elia Beniash, Samuel I. Stupp, SCIENCE, vol. 294, 1684-1688 (2001)
[Non-patent Document 4]
 Shinji Matsumoto, Itaru Hamachi, Dojin News, No. 118, 1-16 (2006)
[Non-patent Document 5]
 Kjeld J. C. Van Bommel et al., Angew. Chem., Int. Ed., vol. 43, 1663-1667 (2004)

DISCLOSURE OF THE INVENTION

Problems to be Solved by the Invention

In a related-art hydrogel, for forming a synthetic polymer gel of the hydrogel, or depending on the case, for gelling a natural polymer such as a gelatin (collagen), a crosslinker having an aldehyde group is necessary to be used.

In addition, for imparting functions, needless to say to a natural polymer gel, to a (synthetic) polymer gel, a copolymerization reaction is necessary to be effected for chemically modifying a polymer chain or for introducing a functional molecule.

Thus, a related-art hydrogel has such problems that the preparation of the gel is cumbersome and that an unreacted crosslinker or unreacted substances during the copolymerization reaction remain.

In addition, in the case (1.) where the above described hydrogelators for forming a non-covalent gel which have been disclosed hitherto, have the amphipathic low molecular weight molecule as the skeleton, depending on the liquid property of the medium, the gel formation may not be achieved. In other words, in an alkaline range, a reaction mixture forms a micelle to become an emulsified liquid. On the other hand, although in an acidic range, the low molecular weight molecules are self-assembled in a fiber shape and a hydrogel can be obtained, there is disclosed substantially no example in which the hydrogelation is achieved in a neutral range regarded as safe for the organism. In addition, the related-art hydrogel also has a problem that an anxiety is left with respect to the safety of a quaternary ammonium cation (for example, Patent Document 1) and the like for the organism environment.

In addition, in the case (2.) where the hydrogelators have a skeleton in the motif of intravital components, the agents have such a problem concerning the productivity that they are not suitable for the mass production and a problem that the gel forming ability depends on a temperature and pH.

Further, in the case (3.) where the hydrogelators have a semi-artificial low molecular weight molecule as the skeleton, for example, referring to a reaction scheme (FIG. 1) for synthesizing a glycoside amino acid derivative constituting the hydrogelator which is described in Patent Document 2, there is specified that sodium azide having high toxicity is used, or for self-assembling a hollow fiber described in Patent Document 3, it is essential to add a transition metal (ion), so that these examples leave a problem concerning biocompatibility and the environmental safety.

Thus, various non-covalent hydrogels and hydrogelators for forming the gels which have been hitherto disclosed are those for which further improvements are required in terms of the gel forming ability (gel structure retaining ability), the safety for the organism environment and the like.

Further, from the viewpoint of the safety for the organism environment, there is a potential requirement for a hydrogelator capable of forming a gel with a smaller adding amount.

In order to solve the problems described above, it is an object of the present invention to provide a novel lipid peptide, particularly a lipid peptide useful as a hydrogelator having high hydrogelling ability capable of forming a hydrogel with an extremely small amount thereof over a wide liquid property range from acidic to alkaline, particularly even in a neutral range.

It is another object of the present invention to provide a hydrogel retaining a gel structure stably over a wide liquid property range from acidic to alkaline using the lipid peptide, and having high environmental suitability, biocompatibility and biodegradability.

Means for Solving the Problems

As a result of assiduous research intended to overcome these disadvantages, the present inventors have found the present invention.

That is, according to a first aspect, a lipid peptide represented by Formula (1):

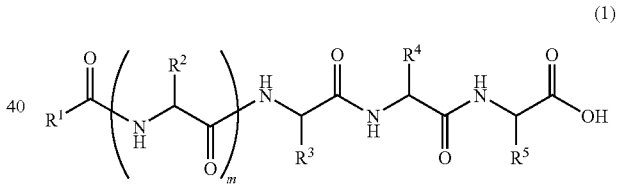

(where $R^1$ represents an aliphatic group having 9 to 23 carbon atoms; $R^2$, $R^3$, $R^4$ and $R^5$ independently represent a hydrogen atom, an alkyl group having 1 to 7 carbon atom(s) which may have a branched chain having 1 to 3 carbon atom(s), a phenylmethyl group, a phenylethyl group or a $-(CH_2)_n-X$ group, and at least one of $R^2$, $R^3$, $R^4$ and $R^5$ represents a $-(CH_2)_n-X$ group; n represents the number of 1 to 4; X represents an amino group, a guanidino group, a $-CONH_2$ group or a 5-membered ring, a 6-membered ring or a fused heterocyclic ring composed of a 5-membered ring and a 6-membered ring which may have 1 to 3 nitrogen atom(s); and m represents 1 or 2), and a pharmaceutically usable salt thereof.

According to a second aspect, the lipid peptide and the pharmaceutically usable salt thereof according to the first aspect, characterized in that $R^1$ represents a straight chain aliphatic group having 11 to 23 carbon atoms which may have 1 to 2 unsaturated bond(s).

According to a third aspect, the lipid peptide and the pharmaceutically usable salt thereof according to the first aspect or the second aspect, characterized in that: $R^2$, $R^3$, $R^4$ and $R^5$ independently represent a hydrogen atom, an alkyl group having 1 to 4 carbon atom(s) which may have a branched chain having 1 or 2 carbon atom(s), a phenylmethyl group or a —$(CH_2)_n$—X group, and one or two of $R^2$, $R^3$, $R^4$ and $R^5$ represent(s) a —$(CH_2)_n$—X group; n represents the number of 1 to 4; X represents an amino group, a guanidino group, a —$CONH_2$ group or a 5-membered ring or a fused heterocyclic ring composed of a 5-membered ring and a 6-membered ring which may have 1 or 2 nitrogen atom(s).

According to a fourth aspect, the lipid peptide and the pharmaceutically usable salt thereof according to the third aspect, characterized in that: $R^2$, $R^3$, $R^4$ and $R^5$ independently represent a hydrogen atom, an alkyl group having 1 to 4 carbon atom(s) which may have a branched chain having 1 or 2 carbon atom(s), a phenylmethyl group or a —$(CH_2)_n$—X group, and one or two of $R^2$, $R^3$, $R^4$ and $R^5$ represent(s) a —$(CH_2)_n$—X group; n represents the number of 1 to 4; X represents an amino group, a guanidino group, a —$CONH_2$ group, a pyrrolyl group, an imidazolyl group, a pyrazolyl group or an indolyl group.

According to a fifth aspect, the lipid peptide and the pharmaceutically usable salt thereof according to the fourth aspect, characterized in that $R^2$, $R^3$, $R^4$ and $R^5$ independently represent a hydrogen atom, a methyl group, an ethyl group, an n-propyl group, an isopropyl group, an n-butyl group, an isobutyl group, a sec-butyl group, a tert-butyl group, a phenylmethyl group, an aminomethyl group, a 2-aminoethyl group, a 3-aminopropyl group, a 4-aminobutyl group, a carbamoylmethyl group, a 2-carbamoylethyl group, a 3-carbamoylpropyl group, a 2-guanidinoethyl group, a 3-guanidinopropyl group, a pyrrolylmethyl group, an imidazolylmethyl group, a pyrazolylmethyl group or a 3-indolylmethyl group, and one or two of $R^2$, $R^3$, $R^4$ and $R^5$ represent(s) an aminomethyl group, a 1-aminoethyl group, a 3-aminopropyl group, a 4-aminobutyl group, a carbamoylmethyl group, a 2-carbamoylethyl group, a 3-carbamoylpropyl group, a 2-guanidinoethyl group, a 3-guanidinopropyl group, a pyrrolylmethyl group, an imidazolylmethyl group, a pyrazolylmethyl group or a 3-indolylmethyl group.

According to a sixth aspect, the lipid peptide and the pharmaceutically usable salt thereof according to the fifth aspect, characterized in that $R^2$, $R^3$, $R^4$ and $R^5$ independently represent a hydrogen atom, a methyl group, an isopropyl group, an isobutyl group, a sec-butyl group, a phenylmethyl group, a 4-aminobutyl group, a carbamoylmethyl group, a 2-carbamoylethyl group, a 3-guanidinopropyl group, an imidazolylmethyl group or a 3-indolylmethyl group, and one or two of $R^2$, $R^3$, $R^4$ and $R^5$ represent(s) a 4-aminobutyl group, a carbamoylmethyl group, a 2-carbamoylethyl group, a 3-guanidinopropyl group, an imidazolylmethyl group or a 3-indolylmethyl group.

According to a seventh aspect, a fiber formed by self-assembly of the lipid peptide and the pharmaceutically usable salt thereof as described in any one of the first aspect to the sixth aspect.

According to an eighth aspect, a hydrogel containing the lipid peptide and the pharmaceutically usable salt thereof as described in any one of the first aspect to the sixth aspect or the fiber as described in the seventh aspect, and an aqueous solution or an alcohol aqueous solution.

Effects of the Invention

The lipid peptide of the present invention can form a hydrogel by gelling an aqueous solution or an alcohol aqueous solution without using a crosslinker or the like required during the formation of a related-art hydrogel, so that no unreacted crosslinker remains. In addition, the lipid peptide of the present invention contains low molecular weight compounds, so that it can form a hydrogel without containing unreacted substances of functional molecules introduced into a related-art hydrogelator for developing functions.

In addition, the lipid peptide of the present invention can form a hydrogel over a wide range of liquid properties from an acidic range to an alkaline range. Particularly, from the viewpoint of high safety required for a cell culture base material, medical materials or the like, the lipid peptide of the present invention having a gel forming ability even in a neutral range is useful as a hydrogelator in the above applications.

In addition, the lipid peptide of the present invention can form a hydrogel only with a small adding amount of 0.03 to 1% by mass, and applies low load to the environment and the organism when the lipid peptide is taken therein.

Further, the lipid peptide of the present invention can form a hydrogel even when a dispersion medium of the lipid peptide contains up to around 50% by volume of an alcohol solvent such as ethanol, so that it can be preferably used in hydrogel applications requiring sterilizing property.

In addition, the lipid peptide of the present invention is an artificial low molecular weight compound composed of only lipid and a peptide and using no animal-derived material (such as collagen, gelatin and matrigel) which is recently leading to a problem of BSE infection or the like, so that the hydrogel obtained therefrom causes no problem of the infection or the like. Moreover, a lipid peptide can be produced only by an amidation reaction of lipid and a peptide without using a reagent having a high reactivity, however, also having toxicity such as sodium azide, so that it can be preferably used as a gelling agent having high safety.

In addition, the lipid peptide of the present invention can also be used as besides the above applications, a protection from a cell damage and a Langmuir monolayer.

In addition, with respect to the fiber of the present invention, when the lipid peptide is self-assembled, a peptide moiety (amino acid) becomes positioned in the outermost side (that is, the fiber surface), so that when the fiber is taken into an organism, the fiber is unlikely to cause a rejection against organism cells and is excellent in cell-adhesiveness. Therefore, the fiber can be preferably used in a medical time-release carrier and an absorbent, a scaffolding for the regeneration medicine and the like.

The fiber is useful as: besides the above applications, a stabilizer, dispersant and humectant in the food industry, agroforestry, cosmetics field and fiber industry; nano-parts in which metals or conductive materials are doped in the electronics and information field; and materials for a filter and conductive materials.

Then, the hydrogel of the present invention can stably retain a gel structure over a wide range of liquid properties from an acidic range to an alkaline range, particularly even under a neutral condition, so that the hydrogel of the present invention is preferred in applications of materials for the biochemistry such as a cell culture and of medical materials.

In addition, the hydrogel of the present invention can be obtained by adding a smaller amount of a lipid peptide than that for a related-art hydrogel as described above, so that it may be said that the hydrogel of the present invention is a hydrogel having high safety both in the organism and in the environment.

Further, the hydrogel of the present invention can stably retain a gel structure even when the dispersion medium of the hydrogel contains up to around 50% by volume of an alcohol solvent such as ethanol, so that the hydrogel of the present invention can be preferably used in applications requiring sterilizing properties.

Further, as described above, when a hydrogel obtained from a lipid peptide which is a low molecular weight compound is used in an external environment, for example in the soil, the hydrogel is easily degraded by soil bacteria or the like, or when the hydrogel is used in an organism, the hydrogel is easily degraded by metabolic enzyme, so that it applies low load to the environment and the organism.

BEST MODES FOR CARRYING OUT THE INVENTION (Lipid Peptide)

The lipid peptide of the present invention has a structure represented by Formula (1):

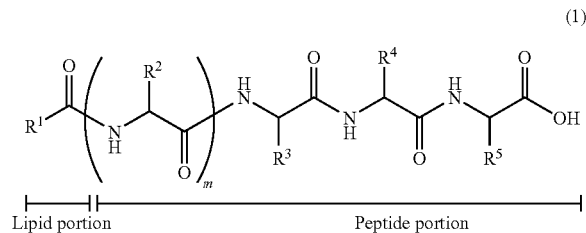

and is composed of a lipid moiety (an alkylcarbonyl group) having a long chain with high lipophilicity and a peptide moiety (tetrapeptide or pentapeptide).

In Formula (1), it is desired that $R^1$ contained in the lipid moiety represents an aliphatic group having 9 to 23 carbon atoms, preferably a straight chain aliphatic group having 11 to 23 carbon atoms which may have one or two unsaturated bond(s).

Particularly preferred specific examples of the structure of the lipid moiety composed of $R^1$ and a carbonyl group adjacent thereto include a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, a vaccenoyl group, an octadecylcarbonyl group, an arachidoyl group, an eicosylcarbonyl group, a behenoyl group, an erucanoyl group, a docosylcarbonyl group, a lignoceroyl group and a nervonoyl group and among them, more preferred are a lauroyl group, a myristoyl group, a palmitoyl group, a margaroyl group, an elaidoyl group, a stearoyl group, an arachidoyl group and a behenoyl group.

In Formula (1), $R^2$, $R^3$, $R^4$ and $R^5$ contained in the peptide moiety independently represent a hydrogen atom, an alkyl group having 1 to 7 carbon atom(s) which may have a branched chain having 1 to 3 carbon atom(s), a phenylmethyl group, a phenylethyl group or a $-(CH_2)_n-X$ group, and at least one, preferably one or two of $R^2$, $R^3$, $R^4$ and $R^5$ represent(s) a $-(CH_2)_n-X$ group; and m represents 1 or 2.

In the $-(CH_2)_n-X$ group, n represents the number Of 1 to 4; X represents an amino group, a guanidino group, a $-CONH_2$ group or a 5-membered ring, a 6-membered ring or a fused heterocyclic ring composed of a 5-membered ring and a 6-membered ring which may have 1 to 3 nitrogen atom(s).

The alkyl group having 1 to 7 carbon atom(s) which may have a branched chain having 1 to 3 carbon atom(s) is preferably an alkyl group having 1 to 4 carbon atom(s) which may have a branched chain having 1 or 2 carbon atom(s).

Specific examples of the alkyl group having 1 to 4 carbon atom(s) which may have a branched chain having 1 or 2 carbon atom(s) include a methyl group, an ethyl group, an n-propyl group, an isopropyl group, an n-butyl group, an isobutyl group, a sec-butyl group or a tert-butyl group, and among them, preferred are a methyl group, an isopropyl group, an isobutyl group or a sec-butyl group.

In the $-(CH_2)_n-X$ group, X represents preferably an amino group, a guanidino group, a $-CONH_2$ group, a pyrrolyl group, an imidazolyl group, a pyrazolyl group or an indolyl group.

Accordingly, the $-(CH_2)_n-X$ group represents preferably an aminomethyl group, a 2-aminoethyl group, a 3-aminopropyl group, a 4-aminobutyl group, a carbamoylmethyl group, a 2-carbamoylethyl group, a 3-carbamoylpropyl group, a 2-guanidino group, a 3-guanidinopropyl group, a pyrrolylmethyl group, an imidazolylmethyl group, a pyrazolylmethyl group or a 3-indolylmethyl group, more preferably a 4-aminobutyl group, a carbamoylmethyl group, a 2-carbamoylethyl group, a 3-guanidinopropyl group, an imidazolylmethyl group or a 3-indolylmethyl group.

In the compound represented by Formula (1), as a particularly preferred lipid peptide compound, there can be mentioned the compounds formed from the following lipid moieties and peptide moieties (amino acid-assembled portion). Here, the abbreviated names of the amino acids are represented as follows: histidine (His); glycine (Gly); phenylalanine (Phe); valine (Val); isoleucine (Ile); alanine (Ala); arginine (Arg); asparagine (Asn); glutamine (Gln); leucine (Leu); lysine (Lys); and tryptophan (Trp). The peptide moieties (i.e., the tetrapeptide and pentapeptide moieties) described herein include Gly-Gly-Gly-His (SEQ ID NO: 1), Gly-Gly-His-Gly (SEQ ID NO: 2), Gly-His-Gly-Gly (SEQ ID NO: 3), His-Gly-Gly-Gly (SEQ ID NO: 4), Gly-Gly-Gly-Lys (SEQ ID NO: 5), Gly-Gly-Lys-Gly (SEQ ID NO: 6), Gly-Lys-Gly-Gly (SEQ ID NO: 7), Lys-Gly-Gly-Gly (SEQ ID NO: 8), Gly-Gly-Gly-Trp (SEQ ID NO: 9), Gly-Gly-Trp-Gly (SEQ ID NO: 10), Gly-Trp-Gly-Gly (SEQ ID NO: 11), Trp-Gly-Gly-Gly (SEQ ID NO: 12), Gly-Gly-Gly-Arg (SEQ ID NO: 13), Gly-Gly-Gly-Gln (SEQ ID NO: 14), Gly-Gly-Gly-Asn (SEQ ID NO: 15), Gly-Gly-Phe-His (SEQ ID NO: 16), Gly-Gly-Ala-His (SEQ ID NO: 17), Gly-Gly-Ile-His (SEQ ID NO: 18), Gly-Gly-Leu-His (SEQ ID NO: 19), Gly-Gly-Val-His (SEQ ID NO: 20), Gly-Ala-Gly-His (SEQ ID NO: 21), Gly-Val-Gly-His (SEQ ID NO: 22), Gly-Leu-Gly-His (SEQ ID NO: 23), Gly-Ile-Gly-His (SEQ ID NO: 24), Ala-Gly-Gly-His (SEQ ID NO: 25), Val-Gly-Gly-His (SEQ ID NO: 26), Gly-Gly-Gly-His (SEQ ID NO: 27), Gly-Gly-Gly-Gly-Lys (SEQ ID NO: 28), and Gly-Gly-Gly-Gly-Trp (SEQ ID NO: 29), which can each be linked to a lipid moiety as shown in Formula (1) in certain aspects, the lipid peptide compounds described herein can include the following:
N-lauroyl-Gly-Gly-Gly-His, N-lauroyl-Gly-Gly-His-Gly, N-lauroyl-Gly-His-Gly-Gly, N-lauroyl-His-Gly-Gly-Gly, N-lauroyl-Gly-Gly-Gly-Lys, N-lauroyl-Gly-Gly-Lys-Gly, N-lauroyl-Gly-Lys-Gly-Gly, N-lauroyl-Lys-Gly-Gly-Gly, N-lauroyl-Gly-Gly-Gly-Trp, N-lauroyl-Gly-Gly-Trp-Gly, N-lauroyl-Gly-Trp-Gly-Gly, N-Trp-Gly-Gly-Gly, N-lauroyl-Gly-Gly-Gly-Arg, N-lauroyl-Gly-Gly-Gly-Gln, N-lauroyl-Gly-Gly-Gly-Asn, N-lauroyl-Gly-Gly-Phe-His, N-lauroyl-Gly-Gly-Ala-His, N-lauroyl-Gly-Gly-Ile-His, N-lauroyl-Gly-Gly-Leu-His, N-lauroyl-Gly-Gly-Val-His, N-lauroyl-Gly-Ala-Gly-His, N-lauroyl-Gly-Val-Gly-His, N-lauroyl-Gly-Leu-Gly-His, N-lauroyl-Gly-Ile-Gly-His, N-lauroyl-Ala-Gly-Gly-His, N-lauroyl-Val-Gly-Gly-His, N-myristoyl-Gly-Gly-Gly-His, N-myristoyl-Gly-Gly-His-Gly, N-myristoyl-Gly-His-Gly-Gly, N-myristoyl-His-Gly-Gly-Gly, N-myristoyl-Gly-Gly-Gly-Lys, N-myristoyl-Gly-Gly-Lys-Gly, N-myristoyl-Gly-Lys-Gly-Gly, N-myristoyl-Lys-Gly-Gly-Gly, N-myristoyl-Gly-Gly-Gly-Trp, N-myristoyl-Gly-Gly- Trp-Gly, N-myristoyl-Gly-Trp-Gly-Gly, N-myristoyl-Trp-Gly-Gly-Gly, N-myristoyl-Gly-Gly-Gly-Arg, N-myristoyl-Gly-Gly-Gly-Gln, N-myristoyl-Gly-Gly-Gly-Asn, N-myristoyl-Gly-Gly-Phe-His, N-myristoyl-Gly-Gly-Ala-His, N-myristoyl-Gly-Gly-Ile-His, N-myristoyl-Gly-Gly-Leu-His, N-myristoyl-Gly-Gly-Val-His, N-myristoyl-Gly-Ala-Gly-His, N-myristoyl-Gly-Val-Gly-His, N-myristoyl-Gly-Leu-Gly-His, N-myristoyl-Gly-Ile-Gly-His, N-myristoyl-Ala-Gly-Gly-His, N-myristoyl-Val-Gly-Gly-His, N-palmitoyl-Gly-Gly-Gly-His, N-palmitoyl-Gly-Gly-His-Gly, N-palmitoyl-Gly-His-Gly-Gly, N-palmitoyl-His-Gly-Gly-Gly, N-palmitoyl-Gly-Gly-Gly-Lys, N-palmitoyl-Gly-Gly-Lys-Gly, N-palmitoyl-Gly-Lys-Gly-Gly, N-palmitoyl-Lys-Gly-Gly-Gly, N-palmitoyl-Gly-Gly-Gly-Trp, N-palmitoyl-Gly-Gly-Trp-Gly, N-palmitoyl-Gly-Trp-Gly-Gly, N-palmitoyl-Trp-Gly-Gly-Gly, N-palmitoyl-Gly-Gly-Gly-Arg, N-palmitoyl-Gly-Gly-Gly-Gln, N-palmitoyl-Gly-Gly-Gly-Asn, N-palmitoyl-Gly-Gly-Phe-His, N-palmitoyl-Gly-Gly-Ala-His, N-palmitoyl-Gly-Gly-Ile-His, N-palmitoyl-Gly-Gly-Leu-His, N-palmitoyl-Gly-Gly-Val-His, N-palmitoyl-Gly-Ala-Gly-His, N-palmitoyl-Gly-Val-Gly-His, N-palmitoyl-Gly-Lue-Gly-His, N-palmitoyl-Gly-Ile-Gly-His, N-palmitoyl-Ala-Gly-Gly-His, N-palmitoyl-Val-Gly-Gly-His, N-margaroyl-Gly-Gly-Gly-His, N-margaroyl-Gly-Gly-His-Gly, N-margaroyl-Gly-His-Gly-Gly, N-margaroyl-His-Gly-Gly-Gly, N-margaroyl-Gly-Gly-Gly-Lys, N-margaroyl-Gly-Gly-Lys-Gly, N-margaroyl-Gly-Lys-Gly-Gly, N-margaroyl-Lys-Gly-Gly-Gly, N-margaroyl-Gly-Gly-Gly-Trp, N-margaroyl-Gly-Gly-Trp-Gly, N-margaroyl-Gly-Trp-Gly-Gly, N-margaroyl-Trp-Gly-Gly-Gly, N-margaroyl-Gly-Gly-Gly-Arg, N-margaroyl-Gly-Gly-Gly-Gln, N-margaryl-Gly-Gly-Gly-Asn, N-margaryl-Gly-Gly-Phe-His, N-margaryl-Gly-Gly-Ala-His, N-margaryl-Gly-Gly-Ile-His, N-margaryl-Gly-Gly-Leu-His, N-margaryl-Gly-Gly-Val-His, N-margaryl-Gly-Ala-Gly-His, N-margaryl-Gly-Val-Gly-His, N-margaryl-Gly-Leu-Gly-His, N-margaryl-Gly-Ile-Gly-His, N-margaryl-Ala-Gly-Gly-His, N-margaryl-Val-Gly-Gly-His, N-stearoyl-Gly-Gly-Gly-His, N-stearoyl-Gly-Gly-His-Gly, N-stearoyl-Gly-His-Gly-Gly, N-stearoyl-His-Gly-Gly-Gly, N-stearoyl-Gly-Gly-Gly-Lys, N-stearoyl-Gly-Gly-Lys-Gly, N-stearoyl-Gly-Lys-Gly-Gly, N-stearoyl-Lys-Gly-Gly-Gly, N-stearoyl-Gly-Gly-Gly-Trp, N-stearoyl-Gly-Gly-Trp-Gly, N-stearoyl-Gly-Trp-Gly-Gly, N-stearoyl-Trp-Gly-Gly-Gly, N-stearoyl-Gly-Gly-Gly-Arg, N-stearoyl-Gly-Gly-Gly-Gln, N-stearoyl-Gly-Gly-Gly-Asn, N-stearoyl-Gly-Gly-Phe-His, N-stearoyl-Gly-Gly-Ala-His, N-stearoyl-Gly-Gly-Ile-His, N-stearoyl-Gly-Gly-Leu-His, N-stearoyl-Gly-Gly-Val-His, N-stearoyl-Gly-Ala-Gly-His, N-stearoyl-Gly-Val-Gly-His, N-stearoyl-Gly-Leu-Gly-His, N-stearoyl-Gly-Ile-Gly-His, N-stearoyl-Ala-Gly-Gly-His, N-stearoyl-Val-Gly-Gly-His, N-elaidoyl-Gly-Gly-Gly-His, N-elaidoyl-Gly-Gly-His-Gly, N-elaidoyl-Gly-His-Gly-Gly, N-elaidoyl-His-Gly-Gly-Gly, N-elaidoyl-Gly-Gly-Gly-Lys, N-elaidoyl-Gly-Gly-Lys-Gly, N-elaidoyl-Gly-Lys-Gly-Gly, N-elaidoyl-Lys-Gly-Gly-Gly, N-elaidoyl-Gly-Gly-Gly-Trp, N-elaidoyl-Gly-Gly-Trp-Gly, N-elaidoyl-Gly-Trp-Gly-Gly, N-elaidoyl-Trp-Gly-Gly-Gly, N-elaidoyl-Gly-Gly-Gly-Arg, N-elaidoyl-Gly-Gly-Gly-Gln, N-elaidoyl-Gly-Gly-Gly-Asn, N-elaidoyl-Gly-Gly-Phe-His, N-elaidoyl-Gly-Gly-Ala- His, N-elaidoyl-Gly-Gly-Ile-His, N-elaidoyl-Gly-Gly-Leu-His, N-elaidoyl-Gly-Gly-Val-His, N-elaidoyl-Gly-Ala-Gly-His, N-elaidoyl-Gly-Val-Gly-His, N-elaidoyl-Gly-Lue-Gly-His, N-elaidoyl-Gly-Ile-Gly-His, N-elaidoyl-Ala-Gly-Gly-His, N-elaidoyl-Val-Gly-Gly-His, N-arachidoyl-Gly-Gly-Gly-His, N-arachidoyl-Gly-Gly-His-Gly, N-arachidoyl-Gly-His-Gly-Gly, N-arachidoyl-His-Gly-Gly-Gly, N-arachidoyl-Gly-Gly-Gly-Lys, N-arachidoyl-Gly-Gly-Lys-Gly, N-arachidoyl-Gly-Lys-Gly-Gly, N-arachidoyl-Lys-Gly-Gly-Gly, N-arachidoyl-Gly-Gly-Gly-Trp, N-arachidoyl-Gly-Gly-Trp-Gly, N-arachidoyl-Gly-Trp-Gly-Gly, N-arachidoyl-Trp-Gly-Gly-Gly, N-arachidoyl-Gly-Gly-Gly-Arg, N-arachidoyl-Gly-Gly-Gly-Gln, N-arachidoyl-Gly-Gly-Gly-Asn, N-arachidoyl-Gly-Gly-Phe-His, N-arachidoyl-Gly-Gly-Ala-His, N-arachidoyl-Gly-Gly-Ile-His, N-arachidoyl-Gly-Gly-Leu-His, N-arachidoyl-Gly-Gly-Val-His, N-arachidoyl-Gly-Ala-Gly-His, N-arachidoyl-Gly-Val-Gly-His, N-arachidoyl-Gly-Leu-Gly-His, N-arachidoyl-Gly-Ile-Gly-His, N-arachidoyl-Ala-Gly-Gly-His, N-arachidoyl-Val-Gly-Gly-His, N-behenoyl-Gly-Gly-Gly-His, N-behenoyl-Gly-Gly-His-Gly, N-behenoyl-Gly-His-Gly-Gly, N-behenoyl-His-Gly-Gly-Gly, N-behenoyl-Gly-Gly-Gly-Lys, N-behenoyl-Gly-Gly-Lys-Gly, N-behenoyl-Gly-Lys-Gly-Gly, N-behenoyl-Lys-Gly-Gly-Gly, N-behenoyl-Gly-Gly-Gly-Trp, N-behenoyl-Gly-Gly-Trp-Gly, N-behenoyl-Gly-Trp-Gly-Gly, N-behenoyl-Trp-Gly-Gly-Gly, N-behenoyl-Gly-Gly-Gly-Arg, N-behenoyl-Gly-Gly-Gly-Gln, N-behenoyl-Gly-Gly-Gly-Asn, N-behenoyl-Gly-Gly-Phe-His, N-behenoyl-Gly-Gly-Ala-His, N-behenoyl-Gly-Gly-Ile-His, N-behenoyl-Gly-Gly-Leu-His, N-behenoyl-Gly-Gly-Val-His, N-behenoyl-Gly-Ala-Gly-His, N-behenoyl-Gly-Val-Gly-His, N-behenoyl-Gly-Leu-Gly-His, N-behenoyl-Gly-Ile-Gly-His, N-behenoyl-Ala-Gly-Gly-His, N-behenoyl-Val-Gly-Gly-His, N-lauroyl-Gly-Gly-Gly-Gly-His, N-myristoyl-Gly-Gly-Gly-Gly-His, N-palmitoyl-Gly-Gly-Gly-Gly-His, N-margaroyl-Gly-Gly-Gly-Gly-His, N-stearoyl-Gly-Gly-Gly-Gly-His, N-elaidoyl-Gly-Gly-Gly-Gly-His, N-arachidoyl-Gly-Gly-Gly-Gly-His, N-behenoyl-Gly-Gly-Gly-Gly-His, N-lauroyl-Gly-Gly-Gly-Gly-Lys, N-myristoyl-Gly-Gly-Gly-Gly-Lys, N-palmitoyl-Gly-Gly-Gly-Gly-Lys, N-margaroyl-Gly-Gly-Gly-Gly-Lys, N-stearoyl-Gly-Gly-Gly-Gly-Lys, N-elaidoyl-Gly-Gly-Gly-Gly-Lys, N-arachidoyl-Gly-Gly-Gly-Gly-Lys, N-behenoyl-Gly-Gly-Gly-Gly-Lys, N-lauroyl-Gly-Gly-Gly-Gly-Trp, N-myristoyl-Gly-Gly-Gly-Gly-Trp, N-palmitoyl-Gly-Gly-Gly-Gly-Trp, N-margaroyl-Gly-Gly-Gly-Gly-Trp, N-stearoyl-Gly-Gly-Gly-Gly-Trp, N-elaidoyl-Gly-Gly-Gly-Gly-Trp, N-arachidoyl-Gly-Gly-Gly-Gly-Trp, and N-behenoyl-Gly-Gly-Gly-Gly-Trp.

Among the above compounds, examples of a more preferred lipid peptide compound include N-lauroyl-Gly-Gly-Gly-His, N-lauroyl-Gly-Gly-His -Gly, N-lauroyl-Gly-His-Gly-Gly, N-lauroyl-His-Gly-Gly-Gly, N-lauroyl-Gly-Gly-Gly-Lys, N-lauroyl-Gly-Gly-Lys-Gly, N-lauroyl-Gly-Lys-Gly-Gly, N-lauroyl-Lys-Gly-Gly-Gly, N-lauroyl-Gly-Gly-Gly-Trp, N-lauroyl-Gly-Gly-Trp-Gly, N-lauroyl-Gly-Trp-Gly-Gly, N-lauroyl-Trp -Gly-Gly-Gly, N-myristoyl-Gly-Gly-Gly-His, N-myristoyl-Gly-Gly-His-Gly, N-myristoyl-Gly-His-Gly-Gly, N-myristoyl-His-Gly-Gly-Gly, N-myristoyl-Gly-Gly-Gly-Lys, N-myristoyl-Gly-Gly-Lys-Gly, N-myristoyl-Gly-Lys-Gly-Gly, N-myristoyl-Lys-Gly-Gly-Gly, N-myristoyl-Gly-Gly-Gly-Trp, N-myristoyl-Gly-Gly-Trp-Gly, N-myristoyl-Gly-Trp-Gly-Gly, N-myristoyl-Trp-Gly-Gly-Gly, N-palmitoyl-Gly-Gly-Gly-His, N-palmitoyl-Gly-Gly-His-Gly, N-palmitoyl-Gly-His-Gly-Gly, N-palmitoyl-His-Gly-Gly-Gly, N-palmitoyl-Gly-Gly-Gly-Lys, N-palmitoyl-Gly-Gly-Lys-Gly, N-palmitoyl-Gly-Lys-Gly-Gly, N-palmitoyl-Lys-Gly-Gly-Gly, N-palmitoyl-Gly-Gly-Gly-Trp, N-palmitoyl-Gly-Gly-Trp-Gly, N-palmitoyl-Gly-Trp-Gly-Gly, N-palmitoyl-Trp-Gly-Gly-Gly, N-palmitoyl-Gly-Gly-Gly-Arg, N-palmitoyl-Gly-Gly-Gly-Gln, N-palmitoyl-Gly-Gly-Gly-Asn, N-palmitoyl-Gly-Gly-Phe-His, N-palmitoyl-Gly-Gly-Ala-His, N-palmitoyl-Gly-Gly-Ile-His, N-palmitoyl-Gly-Gly-Leu-His, N-palmitoyl-Gly-Gly-Val-His, N-palmitoyl-Gly-Ala-Gly-His, N-palmitoyl-Gly-Val-Gly-His, N-palmitoyl-Gly-Leu-Gly-His, N-palmitoyl-Gly-Ile-Gly-His, N-palmitoyl-Ala-Gly-Gly-His, N-palmitoyl-Val-Gly-Gly-His, N-margaroyl-Gly-Gly-Gly-His, N-margaroyl-Gly-Gly-His-Gly, N-margaroyl-Gly-His-Gly-Gly, N-margaroyl-His-Gly-Gly-Gly, N-margaroyl-Gly-Gly-Gly-Lys, N-margaroyl-Gly-Gly-Lys-Gly, N-margaroyl-Gly-Lys-Gly-Gly, N-margaroyl-Lys-Gly-Gly-Gly, N-margaroyl-Gly-Gly-Gly-Trp, N-margaroyl-Gly-Gly-Trp-Gly, N-margaroyl-Gly-Trp-Gly-Gly, N-margaroyl-Trp-Gly-Gly-Gly, N-stearoyl-Gly-Gly-Gly-His, N-stearoyl-Gly-Gly-His-Gly, N-stearoyl-Gly-His-Gly-Gly, N-stearoyl-His-Gly-Gly-Gly, N-stearoyl-Gly-Gly-Gly-Lys, N-stearoyl-Gly-Gly-Lys-Gly, N-stearoyl-Gly-Lys-Gly-Gly, N-stearoyl-Lys-Gly-Gly-Gly, N-stearoyl-Gly-Gly-Gly-Trp, N-stearoyl-Gly-Gly-Trp-Gly, N-stearoyl-Gly-Trp-Gly-Gly, N-stearoyl-Trp-Gly-Gly-Gly, N-elaidoyl-Gly-Gly-Gly-His, N-elaidoyl-Gly-Gly-His-Gly, N-elaidoyl-Gly-His-Gly-Gly, N-elaidoyl-His-Gly-Gly-Gly, N-elaidoyl-Gly-Gly-Gly-Lys, N-elaidoyl-Gly-Gly-Lys-Gly, N-elaidoyl-Gly-Lys-Gly-Gly, N-elaidoyl-Lys-Gly-Gly-Gly, N-elaidoyl-Gly-Gly-Gly-Trp, N-elaidoyl-Gly-Gly-Trp-Gly, N-elaidoyl-Gly-Trp-Gly-Gly, N-elaidoyl-Trp-Gly-Gly-Gly, N-arachidoyl-Gly-Gly-Gly-His, N-arachidoyl-Gly-Gly-His-Gly, N-arachidoyl-Gly-His-Gly-Gly, N-arachidoyl-His-Gly-Gly-Gly, N-arachidoyl-Gly-Gly-Gly-Lys, N-arachidoyl-Gly-Gly-Lys-Gly, N-arachidoyl-Gly-Lys-Gly-Gly, N-arachidoyl-Lys-Gly-Gly-Gly, N-arachidoyl-Gly-Gly-Gly-Trp, N-arachidoyl-Gly-Gly-Trp-Gly, N-arachidoyl-Gly-Trp-Gly-Gly, N-arachidoyl-Trp-Gly-Gly-Gly, N-behenoyl-Gly-Gly-Gly-His, N-behenoyl-Gly-Gly-His-Gly, N-behenoyl-Gly-His-Gly-Gly, N-behenoyl-His-Gly-Gly-Gly, N-behenoyl-Gly-Gly-Gly-Lys, N-behenoyl-Gly-Gly-Lys-Gly, N-behenoyl-Gly-Lys-Gly-Gly, N-behenoyl-Lys-Gly-Gly-Gly, N-behenoyl-Gly-Gly-Gly-Trp, N-behenoyl-Gly-Gly-Trp-Gly, N-behenoyl-Gly-Trp-Gly-Gly, N-behenoyl-Trp-Gly-Gly-Gly, N-lauroyl-Gly-Gly-Gly-Gly-His, N-myristoyl-Gly-Gly-Gly-Gly-His, N-palmitoyl-Gly-Gly-Gly-Gly-His, N-margaroyl-Gly-Gly-Gly-Gly-His, N-stearoyl-Gly-Gly-Gly-Gly-His, N-elaidoyl-Gly-Gly-Gly-Gly-His, N-arachidoyl-Gly-Gly-Gly-Gly-His, N-behenoyl-Gly-Gly-Gly-Gly-His, N-lauroyl-Gly-Gly-Gly-Gly-Lys, N-myristoyl-Gly-Gly-Gly-Gly-Lys, N-palmitoyl-Gly-Gly-Gly-Gly-Lys, N-margaroyl-Gly-Gly-Gly-Gly-Lys, N-stearoyl-Gly-Gly-Gly-Gly-Lys, N-elaidoyl-Gly-Gly-Gly-Gly-Lys, N-arachidoyl-Gly-Gly-Gly-Gly-Lys, N-behenoyl-Gly-Gly-Gly-Gly-Lys, N-lauroyl-Gly-Gly-Gly-Gly-Trp, N-myristoyl-Gly-Gly-Gly-Gly-Trp, N-palmitoyl-Gly-Gly-Gly-Gly-Trp, N-margaroyl-Gly-Gly-Gly-Gly-Trp, N-stearoyl-Gly-Gly-Gly-Gly-Trp, N-elaidoyl-Gly-Gly-Gly-Gly-Trp, N-arachidoyl-Gly-Gly-Gly-Gly-Trp and N-behenoyl-Gly-Gly-Gly-Gly-Trp, and examples of the most preferred compound include N-palmitoyl-Gly-Gly-Gly-His, N-palmitoyl-Gly-Gly-His-Gly, N-palmitoyl-Gly-His-Gly-Gly, N-palmitoyl-His-Gly-Gly-Gly, N-palmitoyl-Gly-Gly-Phe-His, N-myristoyl-Gly-Gly-Gly-His, N-stearoyl-Gly-Gly-Gly-His, N-elaidoyl-Gly-Gly-Gly-His, N-lauroyl-Gly-Gly-Gly-His, N-palmitoyl-Gly-Val-Gly-His, N-palmitoyl-Gly-Ile-His, N-palmitoyl-Ala-Gly-Gly-His, N-palmitoyl-Gly-Gly-Gly-Arg, N-palmitoyl-Gly-Gly-Gly-Gln, N-palmitoyl-Gly-Gly-Gly-Lys, N-behenoyl-Gly-Gly-Gly-His and N-palmitoyl-Gly-Gly-Gly-Gly-His.

(Fiber Formed from Lipid Peptide)

When the lipid peptide of the present invention is charged into an aqueous solution or an alcohol aqueous solution, the peptide moiety in Formula (1) forms an intermolecular non-covalent bond through a hydrogen bond and on the other hand, the lipid moiety in Formula (1) is self-assembled so as to be hydrophobically packed to form a cylindrical secondary assembly, that is, a fiber.

For reference, in FIG. 1, there is shown one example of the conceptual diagram of the self-assembly and gelation of the lipid peptide. Molecules of the lipid peptide (a) are assembled with the lipid moiety as its center, which is a hydrophobic portion (b), to form a fiber (c) by the self-assembly.

(Hydrogel)

When the fiber is formed in an aqueous solution or an alcohol aqueous solution, the fiber forms a three-dimensional network structure (for example, refer to (d) in FIG. 1) and further, a non-covalent bond is formed between the hydrophilic portion (peptide moiety) in the fiber surface and an aqueous solvent, and the fiber swells, so that the whole aqueous solution or alcohol aqueous solution is gelled to form a hydrogel.

Although details of a detailed mechanism while forming the hydrogel of the present invention has been not yet clarified, it is estimated that the charge state of the lipid peptide molecule is involved therein.

The lipid peptide of the present invention is an amphoteric compound having a carboxyl group at a C terminal and an amino group derived from a side chain —$(CH_2)_n$—X group in the peptide moiety. It is considered that the ion state of the lipid peptide is in equilibrium among such four states as a state in which only a carboxyl group is anionized, a state in which only an amino group is cationized, a state in which the lipid peptide is ampho-ionized and a state in which both substituents are not ionized.

Taking into consideration the acid dissociation constant of an amino acid residue, it is considered that the following states exist frequently: in the lipid peptide molecule, a terminal amino group derived from a —$(CH_2)_n$—X group in the peptide moiety is positively charged to be cationized in an acidic range; a terminal carboxyl group at a C terminal of the peptide moiety is negatively charged to be anionized in a basic range; and the lipid peptide molecule is ampho-ionized in a neutral range.

When the lipid peptide is ionized, the affinity of the peptide moiety with water is enhanced and the lipid peptide is self-assembled so that a long chain portion which is the hydrophobic portion is distanced from the contact with water to form a nanofiber. At this time, when an ampho-ion state exists dominantly, ion bonds of cations and anions are formed between nanofibers to form a network structure forming a crosslinkage structure. It is considered that by the formation of this network structure; the nanofiber becomes possible to incorporate a larger amount of water, so that excellent hydrogel forming ability is developed.

As described above, the lipid peptide of the present invention can form a stable hydrogel even in a neutral range. In addition, since the lipid peptide of the present invention is a low molecular weight compound, both the lipid peptide and the hydrogel obtained therefrom of the present invention are degradable in the environment and the organism and a lipid peptide and a hydrogel having high biocompatibility can be obtained.

Therefore, the lipid peptide and the hydrogel obtained therefrom of the present invention can be used in materials for various fields such as cell culture base materials, preservation materials for organism molecules such as cells and proteins, base materials for external use, materials for medical use, materials for biochemistry, cosmetics materials, food materials, contact lenses, paper diapers, artificial actuators, and materials for dry-land agriculture. In addition, as a bioreactor carrier such as enzymes, the lipid peptide and the hydrogel obtained therefrom of the present invention can be widely utilized in studies, medicines, analyses and various industries.

Moreover, since the hydrogel of the present invention is a gel formed from a low molecular weight compound (lipid peptide), various functions such as capability of forming a gel that performs a sol-gel conversion by responding to an external stimulation, can be easily imparted to the hydrogel by a design of the compound, without modifying a polymer chain or effecting a copolymerization reaction.

EXAMPLES

Hereinafter, the present invention will be further described in more detail referring to Examples, which should not be construed as limiting the scope of the present invention.
(Abbreviations Used in Example)
The meanings of abbreviations used in the following Examples are as follows.
Gly: glycine
His: histidine
Phe: phenylalanine
Val: valine
Ile: isoleucine
Ala: alanine
Arg: arginine
Gln: glutamine
Lys: lysine
HBTU: 2-(1H-benzotriazole-1-yl)-1,1,3,3-tetramethyluronium-hexafluorophosphate (manufactured by Watanabe Chemical Industries, Ltd.)
HOBt: 1-hydroxy-benzotriazole (manufactured by Wako Pure Chemical Industries, Ltd.)
DMF: dimethylformamide
DCM: dichloromethane
DIEA: N,N-diisopropylethylamine (manufactured by Tokyo Chemical Industry Co., Ltd.)
TFA: trifluoroacetic acid (manufactured by Watanabe Chemical Industries, Ltd.)
TIS: triisopropylsilane (manufactured by Watanabe Chemical Industries, Ltd.)
(Synthesis of Lipid Peptide)
The lipid peptide was synthesized according to the following procedure of an Fmoc solid phase peptide synthesis method. As the resin, mainly used was an amino acid-Barlos Resin. The synthesis was performed under a synthesis scale of 0.3 mmol.

Example 1

Synthesis of N-palmitoyl-Gly-Gly-Gly-His

About 390 mg of His-Barlos Resin (manufactured by Watanabe Chemical Industries, Ltd.) was charged into a PD-10 column and was washed with 5 mL of DCM three times, and next with 5 mL of DMF three times.

Next, into the column, about 270 mg of Fmoc-Gly-OH (manufactured by Watanabe Chemical Industries, Ltd.) and 2.1 mL of a condensing agent solution 1 (in which 3.05 g of HBTU and 1.25 g of HOBt were dissolved in 16 mL of DMF) were charged.

Further, 2.1 mL of a condensing agent solution 2 (in which 2.75 mL of DIEA was dissolved in 14.25 mL of DMF) was charged into the column.

The content of the column was stirred using a vibrator for 30 minutes and then was washed with 5 mL of DMF five times, next with 5 mL of DCM three times and further with 5 mL of DMF three times.

Next, 5 mL of a 20% piperidine/DMF solution was added to the reaction mixture. The resultant mixture was stirred for 1 minute and then, the solution was removed. Subsequently, 5 mL of a 20% piperidine/DMF solution was added again to the reaction mixture. The resultant mixture was stirred for 45 minutes and washed with 5 mL of DMF five times.

Further, 270 mg of Fmoc-Gly-OH and 2.1 mL each of the condensing agent solution 1 and the condensing agent solution 2 were added to the reaction mixture. The resultant mixture was stirred using a vibrator for 20 minutes and then, was washed with 5 mL of DMF five times, next with 5 mL of DCM three times and further with 5 mL of DMF three times.

Next, 5 mL of a 20% piperidine/DMF solution was added to the reaction mixture. The resultant mixture was stirred for 1 minute and then, the solution was removed. Subsequently, 5 mL of a 20% piperidine/DMF solution was added again to the reaction mixture. The resultant mixture was stirred for 45 minutes and was washed with 5 mL of DMF five times.

Once again, 270 mg of Fmoc-Gly-OH and 2.1 mL each of the condensing agent solution 1 and the condensing agent solution 2 were added to the reaction mixture. The resultant mixture was stirred using a vibrator for 20 minutes and then, was washed with 5 mL of DMF five times, next with 5 mL of DCM three times and further with 5 mL of DMF three times.

Next, 5 mL of a 20% piperidine/DMF solution was added to the reaction mixture. The resultant mixture was stirred for 1 minute and then, the solution was removed. Subsequently, 5 mL of a 20% piperidine/DMF solution was added again to the reaction mixture. The resultant mixture was stirred for 45 minutes and washed with 5 mL of DMF five times.

About 230 mg of palmitic acid (manufactured by Tokyo Chemical Industry Co., Ltd.) was charged into the column and thereto, 21 mL each of the condensing agent solution 1 and the condensing agent solution 2 were added, followed by stirring the reaction mixture using a vibrator for 90 minutes.

After the completion of the reaction, the reaction mixture was washed with 5 mL of DMF five times, next with 5 mL of DCM five times and further with 5 mL of methanol five times and then the resin was vacuum-dried over one night.

After the drying, 3.8 mL of TFA and 0.1 mL of TIS were charged into the column and the content of the column was stirred for 1 hour.

To the recovered mixed solution, water was added to separate out a solid and then the product was recovered by suction filtration. The product was lyophilized and then was washed with 4 mL of acetonitrile three times to obtain the objective compound.

FT-MS$^+$m/z calc. for C28H49N6O6 (M+H)$^+$ 565. 37140. Found 565. 3572.

Example 2

Synthesis of N-palmitoyl-Gly-Gly-His-Gly

About 417 mg of Gly-Alko Resin (manufactured by Watanabe Chemical Industries, Ltd.) was charged into a PD-10 column and was washed with 5 mL of DCM three times, next with 5 mL of DMF three times.

Next, into the column, about 558 mg of Fmoc-His(Trt)-OH (manufactured by Watanabe Chemical Industries, Ltd.) and 2.1 mL of the condensing agent solution 1 (in which 3.05 g of HBTU and 1.25 g of HOBt were dissolved in 16 mL of DMF) were charged.

Further, 2.1 mL of the condensing agent solution 2 (in which 2.75 mL of DIEA was dissolved in 14.25 mL of DMF) was charged.

The content of the column was stirred using a vibrator for 45 minutes and then was washed with 5 mL of DMF five times, next with 5 mL of DCM three times and further with 5 mL of DMF three times.

Next, 5 mL of a 20% piperidine/DMF solution was added to the reaction mixture. The resultant mixture was stirred for 1 minute and then the solution was removed. Subsequently, 5 mL of a 20% piperidine/DMF solution was added again to the reaction mixture. The resultant mixture was stirred for 45 minutes and washed with 5 mL of DMF five times.

Further, 270 mg of Fmoc-Gly-OH and 2.1 mL each of the condensing agent solution 1 and the condensing agent solution 2 were added to the reaction mixture. The resultant mixture was stirred using a vibrator for 20 minutes and was then washed with 5 mL of DMF five times, next with 5 mL of DCM three times and further with 5 mL of DMF three times.

Next, 5 mL of a 20% piperidine/DMF solution were added to the reaction mixture. The resultant mixture was stirred for 1 minute and the solution was removed. Subsequently, 5 mL of a 20% piperidine/DMF solution was added again to the reaction mixture. The resultant mixture was stirred for 45 minutes and was washed with 5 mL of DMF five times.

Once again, 270 mg of Fmoc-Gly-OH and 2.1 mL each of the condensing agent solution 1 and the condensing agent solution 2 were added to the reaction mixture. The resultant mixture was stirred using a vibrator for 20 minutes and then was washed with 5 mL of DMF five times, next with 5 mL of DCM three times and further with 5 mL of DMF three times.

Next, 5 mL of a 20% piperidine/DMF solution was added to the reaction mixture. The resultant mixture was stirred for 1 minute and the solution was removed. Subsequently, 5 mL of a 20% piperidine/DMF solution was added again to the reaction mixture. The resultant mixture was stirred for 45 minutes and washed with 5 mL of DMF five times.

About 230 mg of palmitic acid (manufactured by Tokyo Chemical Industry Co., Ltd.) was charged into the column and thereto, 2.1 mL each of the condensing agent solution 1 and the condensing agent solution 2 were added, followed by stirring the reaction mixture using a vibrator for 90 minutes.

After the completion of the reaction, the reaction mixture was washed with 5 mL of DMF five times, next with 5 mL, of DCM five times and further with 5 mL of methanol five times and then the resin was vacuum-dried over one night.

After the drying, 3.8 mL of TFA and 0.1 mL of TIS were charged into the column and the content of the column was stirred for 1 hour.

To the recovered mixed solution, water was added to separate out a solid and then the product was recovered by suction filtration. The product was lyophilized and then was washed with 4 mL of acetonitrile three times to obtain the objective compound.

FT-MS$^+$m/z calc. for $C_{28}H_{49}N_6O_6$ $(M+H)^+$ 565. 37140. Found 565. 4315.

Example 3

Synthesis of N-palmitoyl-Gly-His-Gly-Gly

By substantially the same procedure as in Example 2, that is, by loading 417 mg of Gly-Alko Resin in a column, condensing 270 mg of Fmoc-Gly-OH, 558 mg of Fmoc-His(Trt)-OH and 270 mg of Fmoc-Gly-OH in this order to the Resin by an Fmoc method, and finally effecting a reaction with 230 mg of palmitic acid, the objective compound was obtained.

FT-MS$^+$m/z calc. for $C_{28}H_{49}N_6O_6$ $(M+H)^+$ 565. 37140. Found 565. 4823.

Example 4

Synthesis of N-palmitoyl-His-Gly-Gly-Gly

By substantially the same procedure as in Example 2, that is, by loading 417 mg of Gly-Alko Resin in a column, condensing 270 mg of Fmoc-Gly-OH, 270 mg of Fmoc-Gly-OH and 558 mg of Fmoc-His(Trt)-OH in this order to the Resin by a Fmoc method, and finally effecting a reaction with 230 mg of palmitic acid, the objective compound was obtained.

FT-MS$^+$m/z calc. for $C_{28}H_{49}N_6O_6$ $(M+H)^+$ 565. 37140. Found 565. 3677.

Example 5

Synthesis of N-palmitoyl-Gly-Gly-Phe-His

By substantially the same procedure as in Example 1, that is, by loading 390 mg of His-Barlos Resin in a column, condensing 350 mg of Fmoc-Phe-OH, 270 mg of Fmoc-Gly-OH and 270 mg of Fmoc-Gly-OH in this order to the Resin by a Fmoc method, and finally effecting a reaction with 230 mg of palmitic acid, the objective compound was obtained.

FT-MS$^+$calc. for $C_{28}H_{49}N_6O_6$ $(M+H)^+$ 655. 4I831. Found 655. 4657.

Example 6

Synthesis of N-myristoyl-Gly-Gly-Gly-His

By substantially the same procedure as in Example 1, that is, by loading 390 mg of His-Barlos Resin in a column, condensing 270 mg of Fmoc-Gly-OH, 270 mg of Fmoc-Gly-OH and 270 mg of Fmoc-Gly-OH in this order to the Resin by a Fmoc method, and finally effecting a reaction with 205 mg of myristic acid, the objective compound was obtained.

FT-MS$^+$m/z calc. for $C_{28}H_{49}N_6O_6$ $(M+H)^+$ 537. 34006. Found 537. 3839.

Example 7

Synthesis of N-stearoyl-Gly-Gly-Gly-His

By substantially the same procedure as in Example 1, that is, by loading 390 mg of His-Barlos Resin in a column, condensing 270 mg of Fmoc-Gly-OH, 270 mg of Fmoc-Gly-OH and 270 mg of Fmoc-Gly-OH in this order to the Resin by a Fmoc method, and finally effecting a reaction with 255 mg of stearic acid, the objective compound was obtained.

FT-MS$^+$m/z calc. for $C_{28}H_{49}N_6O_6$ $(M+H)^+$ 593. 40266. Found 593. 4270.

Example 8

Synthesis of N-elaidoyl-Gly-Gly-Gly-His

By substantially the same procedure as in Example 1, that is, by loading 390 mg of His-Barlos Resin in a column, condensing 270 mg of Fmoc-Gly-OH, 270 mg of Fmoc-Gly-OH and 270 mg of Fmoc-Gly-OH in this order to the Resin by a Fmoc method, and finally effecting a reaction with 253 mg of elaidic acid, the objective compound was obtained.

FT-MS⁺m/z calc. for C28H49N6O6 (M+H)⁺ 591. 38701. Found 591. 3803.

Example 9

Synthesis of N-palmitoyl-Gly-Gly-Gly-Gly-His

By substantially the same procedure as in Example 1, that is, by loading 390 mg of His-Barlos Resin in a column, adding 270 mg of Fmoc-Gly-OH four times to the column to be condensed with the Resin by a Fmoc method, and finally effecting a reaction with 230 mg of palmitic acid, the objective compound was obtained.

FT-MS⁺m/z calc. for C28H49N6O6 (M+H)⁺ 622. 39282. Found 622. 4485.

Example 10

Synthesis of N-lauroyl-Gly-Gly-Gly-His

By substantially the same procedure as in Example 1, that is, by loading 163 mg of H-His(Trt)-Trt(2-Cl) Resin in a column, adding 149 mg of Fmoc-Gly-OH, 149 mg of Fmoc-Gly-OH and 149 mg of Fmoc-Gly-OH in this order to the column to be condensed with the Resin by a Fmoc method, and finally effecting a reaction with 125 mg of lauric acid, 43.8 mg of the objective compound was obtained.

¹H-NMR (500 MHz DMSO-$d_6$ δppm): 8.33 (1H, brs, C-2 His), 8.19-8.17 (2H, m, NH His, Gly), 8.14 (1H, t, 3J=5.8 Hz, NH Gly), 8.06 (1H, t, 3J=5.8 Hz, NH Gly), 7.12 (1H, brs, C-4 His), 4.48 (1H, m, α-CH His), 3.73-3.69 (6H, m, α-CH Gly), 3.05 (1H, m, β-CH2a His), 2.94 (1H, m, β-CH2b His), 2.11 (2H, t, J=7.5 Hz, CH2 Lau), 1.48-1.45 (2H, m, CH2 Lau), 1.23 (16H, brs, CH2 Lau), 0.85 (3H, t, J=7.0 Hz, CH3 Lau);

ESI-MS⁺m/z calc. for C24H41N6O6 (M+H)⁺ 509. 30876. Found 509. 30640.

Example 11

Synthesis of N-palmitoyl-Gly-Val-Gly-His

By substantially the same procedure as in Example 1, that is, by loading 163 mg of H-His(Trt)-Trt(2-Cl) Resin in a column, adding 149 mg of Fmoc-Gly-OH, 170 mg of Fmoc-Val-OH and 149 mg of Fmoc-Gly-OH in this order to the column to be condensed with the Resin by a Fmoc method, and finally effecting a reaction with 160 mg of palmitic acid, 51.1 mg of the objective compound was obtained.

¹H-NMR (500 MHz DMSO-$d_6$ δppm): 8.61 (1H, brs, C-2 His), 8.35 (1H, t, 3J=6.0 Hz, NH Gly), 8.14 (1H, d, 3J=8.0 Hz, NH His), 8.04 (1H, t, 3J=6.0 Hz, NH Gly), 7.82 (1H, d, 3J=8.0 Hz, NH Val), 7.21 (1H, s, C-4 His), 4.52 (1H, m, α-CH His), 4.11 (1H, t-like, J=7.3 Hz, α-CH Val), 3.79-3.65 (4H, m, α-CH Gly), 3.08 (1H, m, β-CH2a His), 2.96 (1H, m, β-CH2b His), 2.12-2.06 (2H, m, CH2 Pal), 1.95 (1H, m, β-CH Val), 1.48-1.42 (2H, m, CH2 Pal), 1.23 (24H, brs, CH2 Pal), 0.88-0.83 (9H, m, CH3 Pal, γ-CH3×2 Val);

ESI-MS⁺m/z calc. for C31H55N6O6 (M+H)⁺ 607. 41831. Found 607. 41583.

Example 12

Synthesis of N-palmitoyl-Gly-Gly-Ile-His

By substantially the same procedure as in Example 1, that is, by loading 163 mg of H-His(Trt)-Trt(2-Cl) Resin in a column, adding 177 mg of Fmoc-Ile-OH, 149 mg of Fmoc-Gly-OH and 149 mg of Fmoc-Gly-OH in this order to the column to be condensed with the Resin by a Fmoc method, and finally effecting a reaction with 160 mg of palmitic acid, 62.0 mg of the objective compound was obtained.

¹H-NMR (500 MHz DMSO-$d_6$ δppm): 8.62 (1H, brs, C-2 His), 8.41 (1H, dm 3J=8.0 Hz, NH His), 8.11 (1H, t, 3J=6.0 Hz, NH Gly), 8.04 (1H, t, 3J=5.8 Hz, NH Gly), 7.84 (1H, d, 3J=8.6 Hz, NH Ile), 7.22 (1H, s, C-4 His), 4.51 (1H, m, α-CH His), 4.15 (1H, t-like, J=8.1 Hz, α-CH Ile), 3.79-3.65 (4H, m, α-CH Gly), 3.10 (1H, m, β-CH2a His), 2.95 (1H, m, β-CH2b His), 2.12 (2H, t, J=7.6 Hz, CH2 Pal), 1.71 (1H, m, β-CH Ile), 1.52-1.45 (2H, m, CH2 Pal), 1.38 (1H, m, γ-CH2a Ile, 1.23 (24H, brs, CH2 Pal), 1.05 (1H, m, γ-CH2b, Ile), 0.87-037 (9H, m, Ch3 Pal, γ-CH3 δ-CH3 Ile);

ESI-MS⁺m/z calc. for C32H57N6O6 (M+H)⁺ 621. 43396. Found 621. 43127.

Example 13

Synthesis of N-palmitoyl-Ala-Gly-Gly-His

By substantially the same procedure as in Example 1, that is, by loading 163 mg of H-His(Trt)-Trt(2-Cl) Resin in a column, adding 149 mg of Fmoc-Gly-OH, 149 mg of Fmoc-Gly-OH and 159 mg of Fmoc-Ala-OH in this order to the column to be condensed with the Resin by a Fmoc method, and finally effecting a reaction with 160 mg of palmitic acid, 27.4 mg of the objective compound was obtained.

¹H-NMR (500 MHz DMSO-$d_6$ δppm): 8.27 (1H, brs, C-2 His), 8.18-8.15 (2H, m, NH His, Gly), 8.12 (1H, t, 3J=5.8 Hz, NH Gly), 8.03 (1H, d, 3J=7.0 Hz, NH Ala), 7.10 (1H, s, C-4 His), 4.47 (1H, m, α-CH His), 4.25 (1H, m, α-CH Ala), 3.73-3.69 (4H, m, α-CH Gly), 3.04 (1H, m, β-CH2a His), 2.93 (1H, m, β-CH2b His), 2.10 (2H, t, J=7.5 Hz, CH2, Pal), 1.50-1.43 (2H, m, CH2 Pal), 1.23 (24H, brs, CH2 Pal), 1.19 (3H, d, J=7.0 Hz, β-CH3 Ala), 0.85 (3H, t, J=7.0 Hz, H3 Pal);

ESI-MS⁺m/z calc. for C29H51N6O6 (M+H)⁺ 579. 38701. Found 579. 38428.

Example 14

Synthesis of N-palmitoyl-Gly-Gly-Gly-Arg

By substantially the same procedure as in Example 1, that is, by loading 202 mg of Fmoc-Arg (Pbf) Resin in a column, adding 149 mg of Fmoc-Gly-OH, 149 mg of Fmoc-Gly-OH and 149 mg of Fmoc-Gly-OH in this order to the column to be condensed with the Resin by a Fmoc method, and finally effecting a reaction with 160 mg of palmitic acid, 21.7 mg of the objective compound was obtained.

¹H-NMR (500 MHz DMSO-$d_6$ δppm); 8.15 (2H, t, 3J=5.8 Hz, NH Gly), 8.08 (1H, t, 3J=5.7 Hz, NH Gly), 7.89 (1H, br, NH Arg), 7.5-6.7 (4H, br, NH2, —NH—×2 Arg), 4.10 (1H, m, α-CH Arg), 3.72 (6H, t-like, J=6.0 Hz, α-CH Gly), 3.09-3.06 (21-1, m, δ-CH2 Arg), 2.12 (2H, t, J=7.5 Hz, CH2 Pal), 1.70 (1H, m, β-CH2a Arg), 1.58 (1H, m, β-CH2b Arg), 1.52-1.43 (4H, m, γ-CH2 Arg, CH2 Pal), 1.24 (24H, brs, CH2 Pal), 0.85 (3H, t, J=6.9 Hz, CH3 Pal);

ESI-MS⁺m/z calc. for C28H54N7O6 (M+H)⁺ 584. 41356. Found 584. 41052.

Example 15

Synthesis of N-palmitoyl-Gly-Gly-Gly-Gln

By substantially the same procedure as in Example 1, that is, by loading 199 mg of H-Gln(Trt) Resin in a column, adding 149 mg of Fmoc-Gly-OH, 149 mg of Fmoc-Gly-OH and 149 mg of Fmoc-Gly-OH in this order to the column to be condensed with the Resin by a Fmoc method, and finally effecting a reaction with 160 mg of palmitic acid, 13.6 mg of the objective compound was obtained.

$^1$H-NMR (500 MHz DMSO-$d_6$ δppm): 8.13 (2H, t, 3J=5.8 Hz, NH Gly), 8.07-8.0 (2H, m, NH Gly, Gln), 7.30 (1H, brs, δ-NH Gln), 6.78 (1H, brs, δ-NH Gln), 4.12 (1H, m, α-CH Gln), 3.75-3.69 (6H, m, α-CH Gly), 2.14-2.07 (4H, m, γ-CH2 Gln, CH2 Pal), 1.93 (1H, m, β-CH$_2$a Gln), 1.77 (1H, m, β-CH2b Gln), 1.51-1.45 (2H, m, CH2 Pal), 1.24 (24H, brs, CH2 Pal), 0.85 (3H, t, J=6.9 Hz, CH3 Pal);

ESI-MS$^+$m/z calc. for C27H50N5O7 (M+H)$^+$ 556. 37103. Found 556. 36859.

Example 16

Synthesis of N-palmitoyl-Gly-Gly-Gly-Lys

By substantially the same procedure as in Example 1, that is, by loading 163 mg of Fmoc-Lys (Boc) Resin in a column, adding 149 mg of Fmoc-Gly-OH, 149 mg of Fmoc-Gly-OH and 149 mg of Fmoc-Gly-OH in this order to the column to be condensed with the Resin by a Fmoc method, and finally effecting a reaction with 160 mg of palmitic acid, 34.3 mg of the objective compound was obtained.

$^1$H-NMR (500 MHz DMSO-$d_6$ δppm): 8.15-8.12 (2H, m, NH Gly), 8.06 (1H, t, J=5.5 Hz, NH Gly), 7.99 (1H, d, J=7.7 Hz, NH Gly), 7.8-7.4 (2H, br, ε-NH2 Lys), 4.17 (1H, m, α-CH Lys), 3.79-3.68 (6H, m, α-CH Gly), 2.76 (2H, t, J=7.5 Hz, ε-CH2 Lys), 2.12 (2H, t, J=7.5 Hz, CH2 Pal), 1.72 (1H, m, β-CH2a Lys), 1.60 (1H, m, β-CH2b Lys), 1.55-1.45 (4H, m, δ-CH2 Lys, CH2 Pal), 1.37-1.30 (2H, m, γ-CH2 Lys), 1.24 (24H, brs, CH2 Pal), 0.85 (3H, t, J=6.9 Hz, CH3 Pal);

ESI-MS$^+$m/z calc. for C28H54N5O6 (M+H)$^+$ 555. 39958. Found 556. 40485.

Example 17

Synthesis of N-behenoyl-Gly-Gly-Gly-His

By substantially the same procedure as in Example 1, that is, by loading 326 mg of H-His(Trt)-Trt(2-Cl) Resin in a column, adding 298 mg of Fmoc-Gly-OH, 298 mg of Fmoc-Gly-OH and 298 mg of Fmoc-Gly-OH in this order to the column to be condensed with the Resin by a Fmoc method, and finally effecting a reaction with 213 mg of behenic acid, 13.7 mg of the objective compound was obtained.

(Evaluation of Hydrogelation of Lipid Peptide with Pure Water)

Lipid peptides synthesized in Examples 10, 12, 13 and 15 to 17 were charged into sample tubes, and pure water (prepared by converting water into an ultrapure water using Milli-Q system (manufactured by Nihon Millipore K.K.)) was added to each sample tube, so that the concentration of the lipid peptide in the aqueous solution becomes 0.5 or 0.1% by mass, followed by heating the content of the sample tube to 90° C. or more to dissolve the lipid peptide and then leaving the resultant solution to cool down.

A state in which, after cooling down, the fluidity of the solution was lost, and when the sample tube was inverted, the solution did not flow down, was evaluated as "gelled" and pH value of the solution at room temperature was measured.

TABLE 1

Evaluation of hydrogelation of lipid peptide by pure water

|  |  | 0.5% (w/v) |  | 0.1% (w/v) |  |
|---|---|---|---|---|---|
|  |  | gelled | pH | gelled | pH |
| Example 10 | N-lauroyl-Gly-Gly-Gly-His | A | 8.0 | A | 7.7 |
| Example 12 | N-palmitoyl-Gly-Gly-Ile-His | A | 7.2 | A | 7.7 |
| Example 13 | N-palmitoyl-Ala-Gly-Gly-His | A | 8.5 | A | 8.2 |
| Example 15 | N-palmitoyl-Gly-Gly-Gly-Gln | A | 8.2 | A | 8.1 |
| Example 16 | N-palmitoyl-Gly-Gly-Gly-Lys | A | 7.2 | A | 7.3 |
| Example 17 | N-behenoyl-Gly-Gly-Gly-His | A | 7.5 | A | 7.4 |

(Evaluation of Hydrogelation of Lipid Peptide by Buffer Solution)

Lipid peptides synthesized in Examples 10 to 17 were charged into sample tubes and five types of phosphate buffer solutions (pH=0, pH=2, pH=7.2, pH=11 and pH=14) were added to the each sample tube so that the concentration of the lipid peptide in the aqueous solution becomes 0.5 or 0.1% by mass, followed by heating the content of the sample tube to 90° C. or more to dissolve the lipid peptide and by leaving the resultant solution to cool down. Here, for the buffer solutions of pH=2 and pH=14, only the lipid peptide aqueous solution having a concentration of 0.5% by mass was evaluated.

A state in which, after cooling down, the fluidity of the solution was lost, and when the sample tube was inverted, the solution did not flow down, was evaluated as "gelled" and pH value of the solution at room temperature was measured. The result is shown in Table 3. In the table, a gelled lipid peptide is indicated by "A"; a lipid peptide which was not gelled is indicated by "B"; and a lipid peptide which was not evaluated is indicated by "-".

TABLE 2

Evaluation of hydrogelation of lipid peptide by phosphate buffer solution

| | pH = 0 | | pH = 2 | | pH = 7.2 | | | | pH = 11 | | | | pH = 14 | |
|---|---|---|---|---|---|---|---|---|---|---|---|---|---|---|
| | 0.5% (w/v) | | 0.5% (w/v) | | 0.5% (w/v) | | 0.1% (w/v) | | 0.5% (w/v) | | 0.1% (w/v) | | 0.5% (w/v) | |
| | Gelled | pH | Gelled | pH | Gelled | pH | Gelled | pH | Gelled | pH | Gelled | pH | Gelled | pH |
| Example 10 | A | — | A | 0.5 | A | — | A | 7.3 | A | 7.4 | A | 9.1 | — | 10.0 | — | 12.7 |
| Example 11 | A | — | — | 0.5 | — | — | A | 7.3 | — | 7.4 | A | 9.1 | — | 10.3 | A | 12.7 |
| Example 12 | A | — | A | 0.5 | A | — | A | 7.3 | A | 7.5 | A | 9.1 | A | 10.2 | — | 12.7 |
| Example 13 | A | — | A | 0.5 | A | — | A | 7.3 | — | 7.5 | — | 9.1 | — | 10.0 | — | 12.7 |
| Example 14 | A | — | A | 0.5 | A | — | A | 7.3 | — | 7.4 | — | 9.1 | — | 10.4 | — | 12.7 |
| Example 15 | — | — | A | 0.4 | A | — | A | 7.3 | — | 7.5 | A | 9.1 | — | 10.4 | — | 12.7 |

TABLE 2-continued

Evaluation of hydrogelation of lipid peptide by phosphate buffer solution

| | pH = 0 | | pH = 2 | | pH = 7.2 | | | | pH = 11 | | | | pH = 14 | |
|---|---|---|---|---|---|---|---|---|---|---|---|---|---|---|
| | 0.5% (w/v) | | 0.5% (w/v) | | 0.5% (w/v) | | 0.1% (w/v) | | 0.5% (w/v) | | 0.1% (w/v) | | 0.5% (w/v) | |
| | Gelled | pH | Gelled | pH | Gelled | pH | Gelled | pH | Gelled | pH | Gelled | pH | Gelled | pH |
| Example 16 | A | 0.5 | A | — | A | 7.3 | A | 7.6 | A | 9.1 | A | 10.3 | — | — |
| Example 17 | — | — | A | — | — | — | — | — | — | 9.1 | — | 10.2 | — | — |

The lipid peptides synthesized in Examples 10, 12, 13 and 15 to 17 in pure water were gelled only at a concentration of 0.1% by mass.

In addition, in the acidic range, the solutions of the lipid peptides synthesized in Examples 10 to 17 were gelled at a concentration of 0.5% by mass. In the neutral range, the solutions of the lipid peptides synthesized in Examples 10 to 16 were gelled at a concentration of 0.5% by mass. In the alkaline range, the solutions of the lipid peptides synthesized in Examples 10 to 12, 15 and 16 were gelled at a concentration of 0.5% by mass.

(Evaluation of Hydrogelation of Lipid Peptide by Metal Ion Aqueous Solution)

A lipid peptide (N-palmitoyl-Gly-Gly-Gly-His) synthesized in Example 1 was charged into sample tubes and five types of 50 mM metal ion aqueous solutions (NaCl aqueous solution, $MgCl_2$ aqueous solution, $CaCl_2$ aqueous solution, $NiCl_2$ aqueous solution, $FeCl_3$ aqueous solution) were added to each sample tube so that the concentration of the lipid peptide in the aqueous solution becomes 0.2% by mass, followed by heating the content of the sample tube to 60° C. or more to dissolve the lipid peptide and leaving the resultant solution to cool down.

After cooling down, the content of the sample tube was observed. It was found that every sample had lost the fluidity of the solution and when the sample tube was inverted, the solution did not flow down, so that it was evaluated that every sample was "gelled". In other words, the lipid peptide of Example 1 in the above five different types of metal ion aqueous solutions was gelled at a concentration of 0.2% by mass.

(Evaluation of Hydrogelation of Lipid Peptide with Ethanol Solution)

The lipid synthesized in Examples 1 was charged into sample tubes and three types of ethanol solutions (ethanol/water mixed solutions, ethanol concentration=10% by volume, ethanol concentration=30% by volume, ethanol concentration=50% by volume) were added to each sample tube so that the concentration of the lipid peptide in the aqueous solution becomes 0.1% by mass, followed by heating the content of the sample tube to 60° C. or more to dissolve the lipid peptide and leaving the resultant solution to cool down.

After cooling down, the content of the sample tube was observed. It was found that every sample had lost the fluidity of the solution and when the sample tube was inverted, the solution did not flow down, so that it was evaluated that every sample was "gelled". In other words, the lipid peptide of Example 1 in the above three types of ethanol aqueous solutions having different ethanol concentrations was gelled only at a concentration of 0.1% by mass.

(Evaluation of Hydrogelation of Lipid Peptide in Low Concentration)

The lipid peptide synthesized in Examples 1 was charged into sample tubes and four types of solutions (1M hydrochloric acid (pH=0), 50 mM phosphate buffer solution (pH=7.5), 50 mM sodium citrate aqueous solution (pH=8.4), 20% by volume ethanol aqueous solution) were added to each sample tube so that the concentration of the lipid peptide in the aqueous solution becomes 0.03% by mass, followed by heating the content of the sample tube to 60° C. or more to dissolve the lipid peptide and leaving the resultant solution to cool down.

After cooling down, the content of the sample tube was observed. As a result, it was found that every sample had lost the fluidity of the solution and when the sample tube was inverted, the solution did not flow down, so that it was evaluated that every sample was "gelled". In other words, the lipid peptide of Example 1 in the above three types of solutions having three different pH values (pH=0, 7.5 and 8.4) and in an ethanol/water mixed solution was gelled only at a low concentration of 0.03% by mass.

INDUSTRIAL APPLICABILITY

The lipid peptide and the hydrogel obtained therefrom according to the present invention can stably retain a gel structure over a wide liquid property ranging from an acidic range to an alkaline range, particularly even under a neutral condition, and have extremely high biocompatibility, so that the lipid peptide and the hydrogel are suitable for the applications of various functional materials.

For example, from the viewpoint of suitability for the above wide liquid property range, the lipid peptide and the hydrogel are preferred in applications such as cleaning agents (for medicine, living, industry and the like), soiling and gelling agents (cosmetics and other applications for articles of daily use), a gelling agent for a dye stabilizing application, and food additives (for acidic food, alkaline food, neutral food, and the like).

In addition, the lipid peptide and the hydrogel can be applied in a neutral range, as materials for biology and biochemistry such as cell culture basic materials and skin basic materials, and in an acidic range, as basic materials of pharmaceutical preparations such as gastric acid adjusters, enteric coated preparations and biodegradable anti-metabolic agents by the feeling of fullness, as stabilizers and additives during the production of acidic milk beverages containing pectin, etc., or in applications for improving an alkaline soil, or the like.

Further, in an alkaline range, the lipid peptide and the hydro gel can be used as stabilizers and additives, during the production of alkaline beverages and milk beverages, as applications for catalytic reactions using various alkaline enzymes (alkaline protease, alkaline cerase, alkaline amylase, alkaline xylase, alkaline pectate lyase and the like), in industrial applications of alkalophilic bacteria, as gelling agents used in alkaline batteries and the like, as acidic soil ameliorant applications, as basic materials, reaction additives and accelerators in various industrial applications such as bioreactors, cleaning agents and soaps, cosmetics, drug discoveries, and analytic investigations.

BRIEF DESCRIPTION OF THE DRAWINGS

FIG. 1 is a schematic view showing a conceptual diagram of self-assembly and gelation following thereto of a lipid peptide.

The invention claimed is:
1. A hydrogel comprising:
a lipid peptide represented by Formula (1) or a pharmaceutically usable salt thereof:

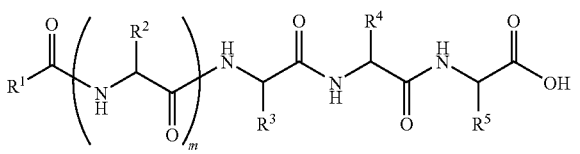

where
R$^1$ represents an aliphatic group having 9 to 23 carbon atoms;
R$^2$, R$^3$, and R$^4$ independently represent a hydrogen atom, an alkyl group having 1 to 7 carbon atom(s) which optionally has a branched chain having 1 to 3 carbon atom(s), a phenylmethyl group, a phenylethyl group, or a —(CH$_2$)$_n$—X group, and R$^5$ represents a —(CH$_2$)$_n$—X group;
n represents a number from 1 to 4;
X represents:
a 5-membered ring,
a 6-membered ring, or
a fused heterocyclic ring composed of a 5-membered ring and a 6-membered ring,
which optionally have 1 to 3 nitrogen atom(s); and
m represents 1 or 2, and
an aqueous solution or an alcohol aqueous solution.

* * * * *